(12) United States Patent
Houzego et al.

(10) Patent No.: US 7,763,014 B2
(45) Date of Patent: *Jul. 27, 2010

(54) INGESTIBLE DEVICE

(75) Inventors: Peter J. Houzego, Cambridge (GB);
Peter N. Morgan, Cambridge (GB);
Peter H. Hirst, Nottinghamshire (GB);
Duncan J. Westland, Cambridge (GB);
Ian R. Wilding, Nottingham (GB)

(73) Assignee: Phaeton Research Ltd. (GB)

( * ) Notice: Subject to any disclaimer, the term of this patent is extended or adjusted under 35 U.S.C. 154(b) by 409 days.

This patent is subject to a terminal disclaimer.

(21) Appl. No.: 11/830,689

(22) Filed: Jul. 30, 2007

(65) Prior Publication Data

US 2007/0270630 A1    Nov. 22, 2007

Related U.S. Application Data

(60) Continuation of application No. 10/607,721, filed on Jun. 27, 2003, now Pat. No. 7,282,045, which is a division of application No. 09/742,936, filed on Dec. 20, 2000, now Pat. No. 6,632,216.

(30) Foreign Application Priority Data

Dec. 21, 1999 (GB) .................................. 9930000.6

(51) Int. Cl.
*A61K 9/22* (2006.01)
(52) U.S. Cl. ................................... 604/890.1
(58) Field of Classification Search ............. 604/93.01, 604/113, 890.1, 892.2, 65–67, 131; 600/2, 600/3, 7
See application file for complete search history.

(56) References Cited

U.S. PATENT DOCUMENTS 3,118,439 A    1/1964   Perrenoud
3,485,235 A    12/1969  Felson (Continued)

FOREIGN PATENT DOCUMENTS

DE            10 76 322        2/1960

(Continued)

OTHER PUBLICATIONS

Century Spring Corp., *Spec Sheet for Compression Spring Part No. 70545* (2003).

(Continued)

*Primary Examiner*—Manuel A Mendez
(74) *Attorney, Agent, or Firm*—Pabst Patent Group LLP

(57) ABSTRACT

An ingestible device for delivering a substance to a chosen location in the GI tract of a mammal includes a receiver of electromagnetic radiation for powering an openable part of the device to an opened position for dispensing of the substance. The receiver includes a coiled wire that couples the energy field, the wire having an air or ferrite core.

In a further embodiment the invention includes an apparatus for generating the electromagnetic radiation, the apparatus including one or more pairs of field coils supported in a housing.

The device optionally includes a latch defined by a heating resistor and a fusible restraint. The device may also include a flexible member that may serve one or both the functions of activating a transmitter circuit to indicate dispensing of the substance; and restraining of a piston used for expelling the substance.

18 Claims, 15 Drawing Sheets

U.S. PATENT DOCUMENTS

| | | | |
|---|---|---|---|
| 3,659,600 | A | 5/1972 | Merrill |
| 4,239,040 | A | 12/1980 | Hosoya et al. |
| 4,425,117 | A | 1/1984 | Hugemann et al. |
| 4,439,197 | A | 3/1984 | Honda et al. |
| 4,507,115 | A | 3/1985 | Kambara et al. |
| 4,844,076 | A | 7/1989 | Lesho et al. |
| 4,869,471 | A | 9/1989 | Schwarz et al. |
| 5,014,004 | A | 5/1991 | Kreibich et al. |
| 5,167,626 | A | 12/1992 | Casper et al. |
| 5,170,801 | A | 12/1992 | Casper et al. |
| 5,196,002 | A | 3/1993 | Hanover et al. |
| 5,217,449 | A | 6/1993 | Yuda et al. |
| 5,279,607 | A | 1/1994 | Schentag et al. |
| 5,639,074 | A | 6/1997 | Greenhill et al. |
| 5,951,594 | A | 9/1999 | Kerver |
| 6,632,216 | B2 | 10/2003 | Houzego et al. |
| 7,282,045 | B2 * | 10/2007 | Houzego et al. ......... 604/890.1 |

FOREIGN PATENT DOCUMENTS

| | | |
|---|---|---|
| DE | 33 39 323 A1 | 2/1985 |
| DE | 40 37 043 | 5/1992 |
| EP | 0 460 327 A1 | 12/1991 |
| EP | 0 715 847 | 6/1996 |
| JP | 58-121938 A | 7/1983 |
| WO | WO 92/21307 | 12/1992 |

OTHER PUBLICATIONS

Connell, et al., "Wireless telemetering from the digestive tract," *Gastroen Technology* 1:266 & 272 (1960).

Cook, et al., "Non-invasive site absorption studies of an aldosterone antagonist (SC-66110) in beagles using a remote control capsule (InteliSite®) and gamma scintigraphy," *Pharm. Sci. Suppl.* 1(1): S-139 (1998).

Digenis, et al., "Acceleration of pharmaceutical research and development with application of gamma scintigraphy," *Eur. Pharm. Contractor*, pp. 22-32 (1999).

Digenis, et al., "Gamma scintigraphy: an evolving technology in pharmaceutical formulation development—Part 1," *Pharm. Sci. & Tech. Today* 1(3): 100-107 (1998).

Digenis, et al., "Gamma scintigraphy: an evolving technology in pharmaceutical formulation development—Part 2," *Pharm. Sci. & Tech. Today* 1(4): 160-165 (1998).

Doll, et al., "A bioavailability study of leuprolide acetate directly released in the ileum and colon of healthy human subjects using gamma scintigraphy and the InteliSite® capsule," *Pharm. Res.* 14(9): S-654 (1997).

Electronic ID, Inc., "Destron-Fearing Electronic ID Background," http://www.electronicidinc.com/eidback.html, pp. 1-3.

Eriksen, et al., "Equipment and methodology for relating gastrointestinal absorption to site of drug release," *J. Pharm. Sci.* 49: 151-156 (1960).

Farrar, et al., "Pressure-sensitive telemetering capsule for study of gastrointestinal motility," *Science* 26(8):975-976 (1957).

Farrar, et al., "Recording of intraluminal gastrointestinal pressures by a radiotelemetering capsule," *Gastroenterology* 36(6):603-612 (1958).

Farrar, et al., "Telemetering of physiologic information from the gastro-intestinal tract by an externally energized capsule" *Proceedings of the International Conference on Medical Electronics*, 3$^{rd}$ Conference pp. 120-121 (1961).

Gardner, et al., "Noninvasive methodology for assessing regional drug absorption from the gastrointestinal tract," *Pharm. Tech.*, pp. 82-89 (1997).

Jacobson, "A critical review of techniques for telemetering physiological date from the alimentary canal," presented at the Third International Conference on Medical Electronics, Jul. 27, 1960.

Lambert, et al., "Autonomous telemetric capsule to explore the small bowel," *Medical & Biological Engineering & Computing* 29(2):191-196 (1991).

Lewin, et al., "Telemetering of the E.E.G from the conscious animal," presented at the Third International Conference on Medical Electronics, Jul. 27, 1960.

McCall, "Receiver systems for use with radio pills" pp. 124-125 *Proceedings of the International Conference on Medical Electronics*, 3$^{rd}$ Conference pp. 124-125(1961).

Mueller, et al., "Two novel techniques for enhancing powering and control of multiple inductively-powered biomedical implants," *IEEE International Symposium on Circuits & Systems* pp. 289-292 (1997).

Mussivand, et al., "A transcutaneous energy and information transfer system for implanted medical devices," *ASAIO Journal* 41(3):253-258 (1995).

Parr, et al., "Evaluation of a prototype remote drug delivery capsule (RDDC) in healthy adult volunteers for non-invasive regional drug absorption studies in the GI tract of man," *Pharm. Res.* 14(9): S-654 (1997).

Parr, et al., "Evaluation of the feasibility and use of a prototype remote drug delivery capsule (RDDC) for non-invasive regional drug absorption studies in the GI tract of man and beagle dog," *Pharm. Res.* 16(2): 266-271 (1999).

Pithavala, et al., "Use of the InteliSite® capsule to study ranitidine absorption from various sites within the human intestinal tract," *Pharm. Res.* 15(12): 1869-1875 (1998).

Rowlands, et al., "Application of electronic techniques to the study of diseases of the gastro-intestinal tract," presented at the Third International Conference of Medical Electronics, Jul. 27, 1960.

Rowlands, et al., "The radio pill—Telemetering from the digestive tract," *British Communications and Electronics*, Aug. 1960.

Russ & Wolff, "Constructional aspects of radio pill suitable for mass production," proceedings of the Third International Conference on Medical Electronics, London, Jul. 21-27, 1960.

Sandefer, "Contributions of gamma scintigraphy to the in vivo evaluation of oral dosage forms: implications of gastrointestinal transit times and the effect on drug absorption," *Doctoral Dissertation, University of Kentucky College of Pharmacy* (1996).

Smalley Steel Ring Company, "Wave Springs" http://www.smalley.com/spring.asp.

Staib, et al., "Measurement of theophylline absorption from different regions of gastro-intestinal tract using a remote controlled drug delivery device" *Eur. J. of Clin. Pharmacol.* 30:691-697 (1986).

Von Ardene, et al., "Uber einen verschluckbaren Intestinalsender," *Zschr. inn. Med* 13(8):269-274 (1958).

* cited by examiner

BEFORE OPENING

AFTER OPENING $\alpha_2 > \alpha_1$

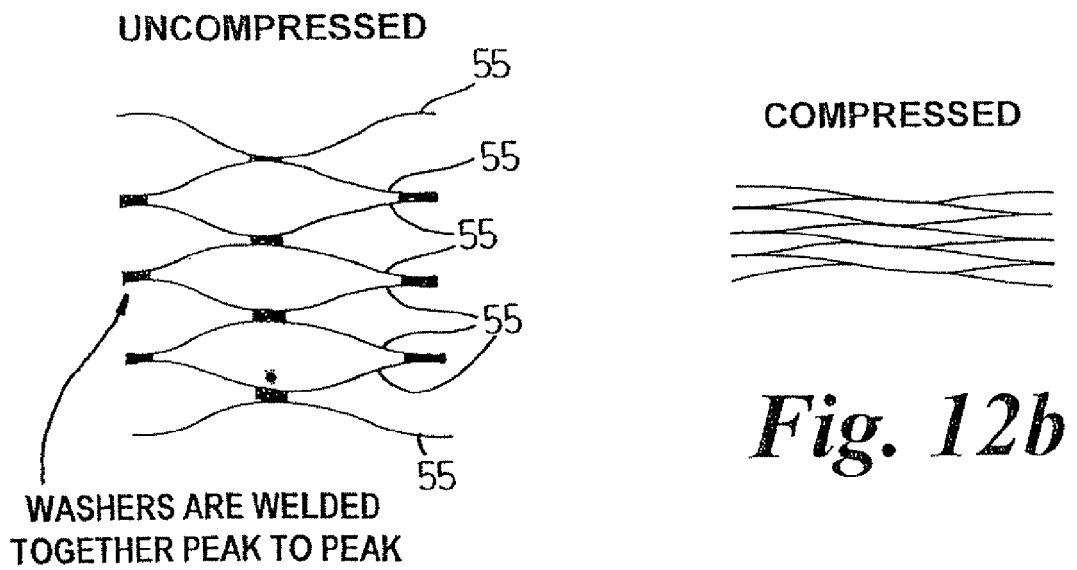
Fig. 12a
Fig. 12b
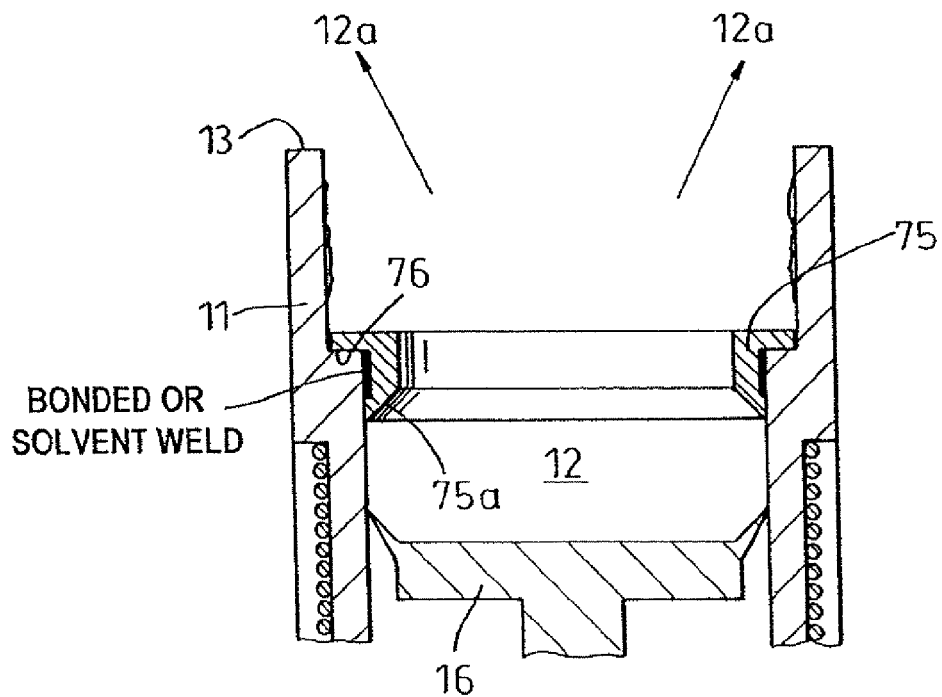
Fig. 13

INGESTIBLE DEVICE

CROSS-REFERENCE TO RELATED APPLICATIONS

This application is a continuation of U.S. Ser. No. 10/607,721 filed on Jun. 27, 2003, which is a divisional of U.S. Ser. No. 09/742,935 filed Dec. 20, 2000 entitled "Ingestible Device" by Peter J. Houzego, Peter N. Morgan, Peter H. Hirst, Duncan J. Westland, and Ian R. Wilding, which claims priority to Great Britain patent application No. 9930000.6 filed on Dec. 21, 1999.

BACKGROUND OF THE INVENTION

The present invention relates to an ingestible device. In particular the invention relates to such a device in the form of a capsule that is intended to release a controlled quantity of a substance, such as a pharmaceutically active compound, foodstuff, dye, radiolabelled marker, vaccine, physiological marker or diagnostic agent at a chosen location in the gastrointestinal (GI) tract of a mammal. Such a capsule is sometimes referred to as a "Site-Specific Delivery Capsule", or SSDC.

SSDC's have numerous uses. One use of particular interest to the pharmaceutical industry involves assessing the absorption rate and/or efficacy of a compound under investigation, at various locations in the GI tract. Pharmaceutical companies can use data obtained from such investigations, eg. to improve commercially produced products.

Several designs of SSDC are known. One design of capsule intended for use in the GI tract of a mammal is disclosed in "Autonomous Telemetric Capsule to Explore the Small Bowel", Lambert et al, Medical & Biological Engineering and Computing, March 1991. The capsule shown therein exhibits several features usually found in such devices, namely:

a reservoir for a substance to be discharged into the GI tract;
an on-board energy source;
a mechanism, operable under power from the energy source, for initiating discharge of the substance from the reservoir;
a switch, operable remotely from outside the body of the mammal, for initiating the discharge; and
a telemetry device for transmitting data indicative of the status, location and/or orientation of the capsule.

Also, of course, the dimensions of the capsule are such as to permit its ingestion via the oesophagus; and the external components of the capsule are such as to be biocompatible for the residence time of the capsule within the body.

The capsule disclosed by Lambert et al suffers several disadvantages. Principal amongst these is the complexity of the device. This means that the capsule is expensive to manufacture. Also the complexity means that the capsule is prone to malfunction.

For example, the capsule disclosed by Lambert et al includes a telemetry device that is initially retracted within a smooth outer housing, to permit swallowing of the capsule via the oesophagus. Once the capsule reaches the stomach, gastric juice destroys a gelatin seal retaining the telemetry device within the housing. The telemetry device then extends from the housing and presents a rotatable star wheel that engages the wall of the GI tract. Rotations of the star wheel generate signals that are transmitted externally of the capsule by means of an on-board RF transmitter powered by a battery within the capsule housing.

This arrangement may become unreliable when used in mammals whose GI motility is poor or whose gastric juice composition is abnormal.

There is a risk of malfunction of the rotating part of the telemetry device, and the method of operation of the capsule is generally complex.

The space needed to house the telemetry device within the capsule during swallowing/ingestion is unusable for any other purpose when the telemetry device is extended. Therefore the Lambert et al capsule is not space-efficient. This is a serious drawback when considering the requirement for the capsule to be as small as possible to aid ingestion.

Also the Lambert et al disclosure details the use of a high frequency (>100 MHz) radio transmitter for remotely triggering the release of the substance from the capsule into the GI tract. The use of such high frequencies is associated with disadvantages, as follows:

When power is transmitted to the capsule whilst it is inside the GI tract the energy must pass through the tissue of the mammal that has swallowed the capsule. The transmission of this power through the body of the mammal may result in possible interactions with the tissue which at some power levels may lead to potential damage to that tissue.

The higher the frequency of energy transmission the higher the coupled power for a given field strength. However, as the frequency is increased the absorption of the energy by the body tissue also increases. The guidelines for the exposure of humans to static and time varying electromagnetic fields and radiation for the UK are given in the National Radiological Protection Board (NRPB) publication "Occupational Exposure to Electromagnetic fields: Practical Application of NRPB Guidance" NRPB-R301. This describes two mechanisms of interaction: induced currents and direct heating measured in terms of the SAR (specific energy absorption rate). In general terms the induced current dominates up to 2 MHz above which the SAR effects take over.

SUMMARY OF THE INVENTION

An ingestible device for delivering a substance to a chosen location in the GI tract of a mammal includes a receiver of electromagnetic radiation for powering an openable part of the device to an opened position for dispensing of the substance. The receiver includes a coiled wire that couples the energy field, the wire having an air or ferrite core.

In a further embodiment the invention includes an apparatus for generating the electromagnetic radiation, the apparatus including one or more pairs of field coils supported in a housing.

The device optionally includes a latch defined by a heating resistor and a fusible restraint. The device may also include a flexible member that may serve one or both the functions of activating a transmitter circuit to indicate dispensing of the substance; and restraining of a piston used for expelling the substance.

According to a first aspect of the invention, there is provided an ingestible device for delivering a substance to a chosen or identifiable location in the alimentary canal of a human or animal, comprising an openable reservoir, for the substance, that is sealable against leakage of the substance; an actuator mechanism for opening the reservoir; an energy source, operatively connected for powering the actuator mechanism; a releasable latch for controllably switching the application of power to the actuator from the energy source; and a receiver of electromagnetic radiation, for operating the latch when the receiver detects radiation within a predetermined characteristic range, the receiver including an air core having coiled therearound a wire; characterised in that the coiled wire lies on or is embedded in an outer wall of the device.

This arrangement advantageously permits the use of an oscillating magnetic field as an external energy source for remotely triggering eg. the release of a compound from the capsule. For reasons discussed below, a magnetic field offers advantages over a field including radio waves.

Preferably the housing defined ingestible device for delivering a substance to a chosen or identifiable location in the alimentary canal of a human or animal, comprising an openable reservoir, an actuator mechanism, an energy source, a releasable latch and a receiver of electromagnetic radiation is cylindrical. Other, non-circular section housings eg. polygonal cross sections are possible.

Preferably the dimensions of the coils of the wire are in the range of 8-12 mm and its length is in the range of 10-20 mm. Such dimensions advantageously permit the coils of the wire to form part of a housing, or capsule whose exterior is smooth and appropriately shaped and sized for ready ingestion. The use of a receiver (antenna) is believed to obviate at least some of the space-inefficiency disadvantages of the Lambert et al capsule.

According to a second aspect of the invention there is provided an ingestible device delivering a substance to a chosen or identifiable location in the alimentary canal of a human or animal, comprising an openable reservoir, for the substance, that is sealable against leakage of the substance; an actuator mechanism for opening the reservoir; an energy source, operatively connected for powering the actuator mechanism; a releasable latch for controllably switching the application of power to the actuator from the energy source; and a receiver of electromagnetic radiation, for operating the latch when the receiver detects radiation within a predetermined characteristic range, the device including a ferrite core having coiled therearound a wire for coupling received electromagnetic radiation to the releasable latch, characterised in that the device comprises an elongate, hollow housing, the ferrite core being elongate with its longitudinal axis aligned with the longitudinal axis of the hollow housing.

The ferrite core and coil combination of the ingestible device delivering a substance to a chosen or identifiable location in the alimentary canal of a human or animal, comprising an openable reservoir, for the substance, that is sealable against leakage of the substance; an actuator mechanism for opening the reservoir; an energy source, operatively connected for powering the actuator mechanism; a releasable latch for controllably switching the application of power to the actuator from the energy source; and a receiver of electromagnetic radiation, for operating the latch when the receiver detects radiation within a predetermined characteristic range, the device including a ferrite core having coiled therearound a wire for coupling received electromagnetic radiation to the releasable latch, characterised in that the device comprises an elongate, hollow housing, the ferrite core being elongate with its longitudinal axis aligned with the longitudinal axis of the hollow housing also allows, in an alternative embodiment of the invention, highly efficient coupling of energy from a magnetic field to the circuitry forming part of the capsule. Thus this aspect of the invention allows the construction of an advantageously compact device whose energy efficiency is higher than that of prior art designs.

In preferred embodiments of the invention the receiver includes the ferrite core and coil combination as one of its circuit components. Either embodiment of the apparatus may optionally include a transmitter including a said air or ferrite core and coil combination. The air or ferrite core and coil preferably are spaced from any fluid within or outside the device by 0.1 to 1 mm. The air or ferrite core may have coiled therearound a wire for transmitting electromagnetic radiation.

The preferred operating regime for the device of the invention is between 1 MHz and 14 MHz. In addition to the biological effects there are a number of electromagnetic issues which influence the choice of operating frequency. One issue is restrictions on the use of the electromagnetic spectrum to prevent interference between various users. Thus 13.56 MHz is a preferred operating frequency as this frequency is designated for general industrial use. However, at this, the upper end, of the frequency range several adverse effects occur. These include loading of the transmitter by the body tissue, skin effect adversely affecting the receiver impedance and induction heating of metal objects.

The selected frequency for use of the preferred embodiment of the invention is therefore at the lower end of the range, nominally between 1 MHz and 3.0 MHz.

The frequency effects therefore determine that the power transmitted to the device of the invention to energize the latch comes from a magnetic field of between 1.0 MHz and 3.0 MHz induced over the region of the body containing the capsule. The SSDC of the invention is designed with a means for extracting power from this magnetic field to energize the latch. It should be noted that the magnetic field has no corresponding electric field such as in a radiowave and as such there is energy stored in the field with minimal loss until a receiver is placed within the field capable of extracting the energy.

The preferred embodiment of the receiver is a coil of wire arranged so that the coil intercepts the field lines so that a voltage is induced across the coil by the time varying magnetic field. A capacitor connected across the coil tunes the circuit so that it has a resonant frequency equal to the frequency of the energizing field. When such a tuned receiver is placed in an oscillating magnetic field a high current is induced in the coil and this current generates a magnetic field of its own. It is the interaction of these fields that enables the receiver to extract significant amounts of real power from the energizing magnetic field. The power is accessed by connecting the latch electrical circuit in series or parallel with the coil/capacitor tuned receiver.

The magnitude of the power that can be extracted from the magnetic field is a strong function of the size and shape of the antenna (receiver coil). The voltage induced in the coil is proportional to its area and the power induced is proportional to the square of the voltage. Hence the power that can be extracted from the field is proportional to the fourth power of the diameter of the coil. In practice, the actual power is also modified by the permeability surrounding the coil and a shape factor relating to the length and the angular orientation of the coil to the field.

In a preferred embodiment of the invention an air cored design of receiver antenna has been developed which uses between 60 and 100 turns of copper wire in the range 0.1 mm to 0.3 mm diameter wound as a single or double layer cylindrical coil of diameter between 8 mm and 12 mm and length between 10 mm and 20 mm.

Care must be taken in the design to minimise the effective impedance of the receiver coil in order to maximise the Q of the circuit. Unwanted impedance can be added to the circuit from a number of sources:

Eddy currents in metallic components

Skin depth effects in the conductor

Dielectric loss in the tuning capacitor.

In addition the proximity of a conductive fluid to the coil can change the resonant frequency as it acts as an additional capacitance in parallel to the coil. It is therefore preferable to maintain a minimum separation of the coil from any internal or external fluid. This distance should be in the range of 0.1 mm to 1.0 mm.

According to a third aspect of the invention there is provided an apparatus for transmitting electromagnetic radiation to power an ingestible device, the apparatus comprising a support supporting a pair of transmitter coils including one or more loops operatively connectable to a source of oscillating electrical current, the support supporting the respective coils of the pair on opposite sides of the abdomen of an animal.

More specifically, the preferred approach used in this invention is inductive coupling at a frequency which gives high energy density but at which the absorption by body tissue is small compared to the energy coupled into the capsule. In this approach an alternating current is passed through one or more loops of a conductor such that an alternating magnetic field is generated between the loops. A preferred arrangement is to use two loops, one on either side of the abdomen. With this arrangement the amplitude of the magnetic field at any point between the loops can be accurately controlled. Thus, for example, two loops separated by their radius form a Helmholtz pair giving a nominally uniform field over the full volume between the loops. In the invention the spacing between the loops would be between one radius and four radii. The preferred embodiment has a spacing between the loops equal to the diameter of the loop as this maximises the central field value for a given value of the reactive power of the field generator supply.

It should be noted that a coil pair will generate a combination of magnetic and electrostatic fields around it. The major one of interest is the magnetic field which, in radio terms, only exists in the near field. The design of the field generator uses appropriate shielding to minimise the longer range radio waves and the electrostatic fields.

The energy that can be transmitted by an alternating magnetic field is a function of its field strength, frequency and the mutual inductance between the energizing and receiving coils. The apparatus of the invention optimises those three variables to meet the needs of safe and reliable operation with readily available electronic components.

The use of a pair of current loops to generate the field is chosen to maximise the magnetic field in the useful volume between the loops whilst minimising near field electric field and far field electromagnetic radiation. This minimises any potential effects on persons close to the field generator from the electric field gradient and also minimises stray electromagnetic radiation which could interfere with other electrical equipment.

The maximum power level is achieved when the axis of the coil in the capsule is aligned with the axis of the coil of the external field generator. This cannot be guaranteed when the capsule is inside the GI tract.

In the prior art, arrangements have been made inside the capsule to ensure that the magnetic flux is guided through the receiver coil whatever the orientation. One example of this is the use of 3 orthogonal coils wound around a ferrite core with a 3 axis cross form, as disclosed in U.S. Pat. No. 5,167,626.

Within the size constraints of SSDC's such arrangements are sub-optimal in their efficiency in interacting with the external field as they suffer from poor shape factor. The preferred arrangement in this invention is the use of a single coil geometry which has high efficiency only when the external magnetic field is orientated along its preferred axis and to provide a means of changing the orientation of the energizing field until it aligns with the capsule. Theoretically this can be achieved in a number of ways:

Rotating the mammal with respect to the energizing field

Rotating the field generator with respect to the mammal

Providing a plurality of energizing coils at different angular orientations and energizing them sequentially or in combination to rotate the orientation of the magnetic field in space until it is aligned to the capsule axis.

The preferred embodiment of the invention uses 3 coil pairs mounted orthogonally to each other. The coils are sized to permit eg. a person to be positioned within the space enclosed by the coils. An example of the typical size of the coils would be 600 mm diameter and 600 mm apart.

To facilitate entry of the person to the central region eg. the pair of coils with the vertical axis may be arranged so that part of one of the coils is contained on a door where continuity of the coil is provided by electrical connections on the door when it is closed; or one of the coils may be on a vertical slideway so that the person could stand at the correct location and the coils slid into position by moving vertically.

Another possibility is for the coil pairs to be supported on a wearable garment.

The energization of the magnetic field generator requires powering the field coils with current at the level necessary to generate the field at the required frequency of between 1.0 MHz and 14.0 MHz.

A typical field strength would be in the range 20 $Am^{-1}$ to 200 $Am^{-1}$. To generate this field strength coils with multiple turns can be used where the number of turns is chosen to match the capabilities of the electronic components driving the current. A preferred embodiment of the invention uses 2 turns per coil although other implementations may use from 1 to 10 turns per coil.

In order to minimise resistive heating at these frequencies large diameter conductors or Litz wire are preferred in the construction of the field coils, to minimise the effect of skin depth limiting current penetration into the wire.

The powering of the energizing coils is traditionally accomplished using a circuit comprising a low power oscillator, an r.f. amplifier and a matching network efficiently to couple the coils to the amplifier. Typically the oscillator is crystal controlled for frequency stability. This approach suffers from the problem that changes to the load impedance can reduce the field strength if the tuning of the matching unit becomes sub optimal due to, for example, the electrical effects of a body close to the coils.

In the apparatus of the invention the current is generated by using the field coils as part of the frequency determining components of a power oscillator directly driving the coils. The major advantage of this approach is that the field level remains constant even if the effective load impedance changes. This is achieved at the expense of a small change in frequency.

At the lower end of the preferred frequency range 1.0 MHz to 3.0 MHz the frequency shift caused by the presence or absence of people or small metal objects within the energized field volume is small compared with the bandwidth of the tuned receiver in the capsule and hence there is minimal change in the receiver power. This is considered a major improvement on prior art as it provides more reliable actuation.

The power oscillator can be implemented using any of a range of established oscillator circuits. The preferred embodiment uses a Hartly oscillator and achieves efficient performance by the use of 6 mm diameter copper tube for the coils and low dielectric loss capacitors for the passive components and a low loss, high voltage power MOSFET for the active component.

According to a fourth aspect of the invention there is provided a method of operating an ingestible device for delivering a substance to a chosen or identifiable location in the alimentary canal of a human or animal, causing a mammal to ingest an ingestible device comprising an openable reservoir, for the substance, that is sealable against leakage of the substance; an actuator mechanism for opening the reservoir; an energy source, operatively connected for powering the actuator mechanism; a releasable latch for controllably switching the application of power to the actuator from the energy source; and a receiver of electromagnetic radiation, for operating the latch when the receiver detects radiation within a predetermined characteristic range; the receiver being capable of extracting energy from an oscillating magnetic field and the method comprising at a chosen time, generating at least one axial, oscillating magnetic field and directing the field at the abdomen of the mammal whereby the receiver intercepts the said field and triggers the latch to cause opening of the reservoir; and simultaneously inhibiting the generation of long wave radio waves and short wave electrostatic radiation in the vicinity of the said abdomen. Preferred features of the method are the step of generating two or more axial, oscillating magnetic fields whose axes are mutually skewed; the step of generating two or more axial, oscillating magnetic fields whose axes are mutually skewed and including the step of generating three said fields, wherein the axes of the said fields are mutually orthogonal; and the field is generated using a coil pair operatively connected to a source of an oscillating current.

It is desirable for an SSDC to indicate its location and status when in the GI tract In particular it is important for the SSDC to indicate the precise moment at which the discharge of the substance from the reservoir occurs, and for the SSDC to indicate its location in the GI tract at or close to such a time.

For this reason it is known to include in an SSDC a transmitter that transmits a signal, indicative of the status and, optionally, the location of the SSDC, beyond the body of the mammal. One way of achieving the latter effect is to provide a radiolabelled marker within the SSDC, that may be tracked within the GI tract by means of known Gamma scintigraphy techniques.

U.S. Pat. No. 5,279,607 discloses an SSDC the operation of which is initiated by a receiver and latch combination. The receiver is a tuned resonant circuit, including a first antenna, that generates a current in a heating resistor when it couples, via the antenna, with an oscillating electromagnetic field of the same frequency as the resonant circuit, transmitted from outside the body of the mammal.

The heating resistor is positioned to heat a fusible component that holds a resiliently deformable member in an energy storage (ie. high potential energy) condition. On fusing of the fusible component a diaphragm moves and is ruptured by a pin. This causes two reagents to mix in a reaction chamber and generate a gas, the increasing pressure of which drives a piston to expel the substance from the reservoir of the SSDC.

The SSDC of U.S. Pat. No. 5,279,607 includes a second resonant circuit capable of acting as a transmitter of a signal intended to indicate emptying of the reservoir. The second circuit is initially isolated from the receiver circuit by an electrical short. A blade attached to the piston ruptures the short as it starts to move, thereby coupling the second resonant circuit to the electromagnetic field. This induces a current in the second circuit that is transmitted, via a further antenna, for receipt and processing by a receiver external to the mammal.

The SSDC of U.S. Pat. No. 5,279,607 suffers from the disadvantage that, because of the limited space within the capsule, the breakable short cannot be placed anywhere other than close to the initial position of the piston—otherwise the short may encroach into space intended for storage of the substance; or the blade may be unacceptably large compared with the other components in the capsule.

Consequently the blade in U.S. Pat. No. 5,279,607 of necessity ruptures the short at the beginning of the travel of the piston. This means that the second resonant circuit may generate a signal indicative of discharge of the substance from the reservoir even when the SSDC fails to achieve this, eg. through sticking of the piston or failure of the gas generating reagents to react completely.

Also if, as may be desirable or sometimes unavoidable in an SSDC, it is required to locate the second resonant circuit at a location spaced from the piston or other actuator that causes discharge of the substance, in the SSDC of U.S. Pat. No. 5,279,607 this may only be achieved at the expense of including comparatively long electrical connecting wires between the first circuit, the second circuit and the breakable short. This may complicate the process of assembly of the SSDC.

According to a fifth aspect of the invention there is provided a device for delivering a substance to a chosen or identifiable location in the alimentary canal of a human or animal, comprising an openable reservoir, for the substance, that is sealable against leakage of the substance; an actuator mechanism for opening the reservoir; an energy source, operatively connected for powering the actuator mechanism; a releasable latch for controllably switching the application of power to the actuator mechanism from the energy source; a receiver of electromagnetic radiation, for operating the latch when the receiver detects radiation within a predetermined characteristic range; and a transmitter of electromagnetic radiation for transmitting a signal indicative of operation of the device, the said reservoir including an exit aperture, for the substance, closed by a closure member that is sealingly retained relative to the aperture, the exit aperture being openable on operation of the actuator mechanism; wherein (i) the latch is thermally actuated; (ii) the energy source is held in a potential energy state by the latch until the latch operates; and (iii) the device includes a heater for heating the latch whereby, on the receiver detecting the said radiation the receiver operates to power the heater and thereby release the latch, permitting expulsion of the substance from the reservoir; characterized in that: the device also includes a restraint operable to limit operation of the actuator mechanism; and in that, on release of the latch, the restraint operates a switch to activate the transmitter for transmission of a said signal.

The inclusion of a restraint advantageously permits limiting of the movement or extent of operation of the actuator mechanism.

The use of the restraint to operate the switch confers considerable design freedom on a designer of a device according to the invention. In particular, the switch may be located conveniently close to a transmitter circuit even if the latter is remote from the actuation mechanism.

Preferred features of the fifth aspect of the invention are the actuator mechanism includes a moveable member moveable under power of kinetic energy from the energy source to promote expulsion of the substance from the reservoir; the restraint includes a flexible member interconnecting the moveable member and an anchorage fixed relative to the remainder of the device; and the switch includes a breakable, electrically conductive member, the flexible member and the breakable member being mutually engageable whereby on movement of the moveable member sufficiently partly or completely to expel or initiate expulsion of the substance from the reservoir the flexible member engages and breaks the breakable member to operate the switch; the actuator mechanism includes a piston moveable under power from the energy source for compressing the substance in the reservoir to promote its expulsion therefrom; the transmitter includes a resonant circuit connectable to draw power from the receiver; and the breakable member is an electrical short that electrically isolates the resonant circuit from the receiver until the flexible member breaks the breakable member; the length of the flexible member is such as to limit the travel of the moveable member to a chosen maximum; and the restraint and the switch are so dimensioned and/or located that the restraint operates the switch at a time corresponding to a predetermined amount of movement of the moveable member.

There are various possible approaches to providing an on-board energy source for the device.

In general terms to accomplish sufficient force and movement to expel the drug within a few seconds requires forces in the range 2 to 20N over distances of 2 mm to 20 mm. This typically amounts to a mechanical power level in the order of 0.1 W or an energy of 0.1 J. If the energy were stored in electrical form and used to drive an electromechanical actuator of simple form then typically the conversion efficiency would be less than 10%. An electrical energy storage system would then require to store 1 J of energy and deliver it at 1 W power. Micro-batteries as used in watches are of the necessary size and store easily sufficient energy; however they can only deliver that power at milliwatt rates. Capacitors however can deliver their energy at the required power levels but within the size constraint can only store milliJoules of energy.

Several other forms of energy storage are theoretically possible including:
   Chemical gas generation
   Compressed nitrogen or air
   Liquified propellant fluids (eg. $N_2O$, butane/propane, HFA's)
   Springs
   Chemical heat generation Chemical storage has potentially the highest energy density, but introduces issues associated with chemical compatibility, stability, triggering and toxicological safety.

Within the available space constraints there is sufficient volume to store the required energy either in springs or as a compressed gas, eg. air both of which forms are possible as the energy can be released directly in the desired form of a force acting to cause mechanical motion. However the complexity of a device including a compressed air source may militate against its use.

According to a sixth aspect of the invention there is provided a device for delivering a substance to a chosen or identifiable location in the alimentary canal of a human or animal, comprising an openable reservoir, for the substance, that is sealable against leakage of the substance; an actuator mechanism for opening the reservoir; an energy source, operatively connected for powering the actuator mechanism; a releasable latch for controllably switching the application of power to the actuator from the energy source; and a receiver of electromagnetic radiation, for operating the latch when the receiver detects radiation within a predetermined characteristic range; the energy source including a compressed spring capable of acting on the actuator mechanism the expansion of which is initiatable by the latch and the work of the expansion of which causes operation of the actuator mechanism, characterized in that the spring, in its uncompressed state, has a minimum helical angle of 15°. Preferred features of the sixth aspect of the device are the spring includes a wire whose diameter is approximately 0.8 mm and the spring defines a hollow cylinder.

Another device according to a seventh aspect of the invention is an ingestible device for delivering a substance to a chosen or identifiable location in the alimentary canal of a human or animal, comprising an openable reservoir, for the substance, that is sealable against leakage of the substance; an actuator mechanism for opening the reservoir; an energy source, operatively connected for powering the actuator mechanism; a releasable latch for controllably switching the application of power to the actuator from the energy source; and a receiver of electromagnetic radiation, for operating the latch when the receiver detects radiation within a predetermined characteristic range; the energy source including a compressed spring capable of acting on the actuator mechanism the expansion of which is initiatable by the latch and the work of the expansion of which causes operation of the actuator mechanism, characterized in that the spring includes a pair of wires each coiled in loops to define a pair of hollow cylinder-like shapes, a first said cylinder-like shape being of a greater internal diameter than the outer diameter of the second said cylinder-like shape and the first cylinder-like shape encircling the second cylinder. An eighth aspect of the invention is an ingestible device for delivering a substance to a chosen or identifiable location in the alimentary canal of a human or animal, comprising an openable reservoir, for the substance, that is sealable against leakage of the substance; an actuator mechanism for opening the reservoir; an energy source, operatively connected for powering the actuator mechanism; a releasable latch for controllably switching the application of power to the actuator from the energy source; and a receiver of electromagnetic radiation, for operating the latch when the receiver detects radiation within a predetermined characteristic range; the energy source including a compressed spring the expansion of which is initiatable by the latch and the work of the expansion of which causes operation of the actuator mechanism, characterized in that the spring comprises a stack of resiliently deformable discs, the periphery of each disc having formed therein a series of waves, the waves of respective said discs connecting such that the peak of each wave contacts the trough of a wave of an adjacent said disc.

A device according to a ninth aspect of the invention is an ingestible device for delivering a substance to a chosen or identifiable location in the alimentary canal of a human or animal, comprising an openable reservoir, for the substance, that is sealable against leakage of the substance; an actuator mechanism for opening the reservoir; an energy source, operatively connected for powering the actuator mechanism; a releasable latch for controllably switching the application of power to the actuator from the energy source; a receiver of electromagnetic radiation, for operating the latch when the receiver detects radiation within a predetermined characteristic range; and a transmitter of electromagnetic radiation for transmitting a signal indicative of operation of the device; the said reservoir including an exit aperture, for the substance, closed by a closure member that is sealingly retained relative to the aperture, the exit aperture being openable on operation of the actuator mechanism; wherein (i) the latch is thermally actuated; (ii) the energy source is held in a potential energy state by the latch until the latch operates; and (iii) the device includes a heater for heating the latch whereby, on the receiver-detecting the said radiation the receiver operates to power the heater and thereby release the latch, permitting expulsion of the substance from the reservoir; characterized in that the device also includes (a) a restraint operable to limit operation of the actuator mechanism; (b) a switch for switchably operating the transmitter; and (c) a switch member operatively interconnecting the actuator mechanism and the switch such that operation of the actuator mechanism causes the switch member to operate the said switch.

One preferred embodiment of the device includes a coil spring which operates to move a piston to expel the drug from inside the capsule through an opening at the other end of the capsule. An example of the dimensions and components that could be used would be for a volume of 1 ml available to contain the drug in the form of a cylinder 9 mm in diameter and 16 mm long. A coil spring of 8 mm outer diameter compressed to a length of 4.6 mm could exert an initial force of over 1 kg and have a residual force of 0.2 kg after it has travelled the 16 mm.

BRIEF DESCRIPTION OF THE FIGURES

There now follows a description of preferred embodiments of the invention, by way of non-limiting example, with reference being made to the accompanying drawings in which:

FIGS. 10 to 12 show three kinds of energy source in the form of compression springs;

FIG. 13 shows a restraining ring for retaining moveable components of the device of the invention within its housing, after dispensing of a substance;

FIGS. 18 and 19 show steps in the assembly of the device; and

DETAILED DESCRIPTION OF THE INVENTION

Figure 1:
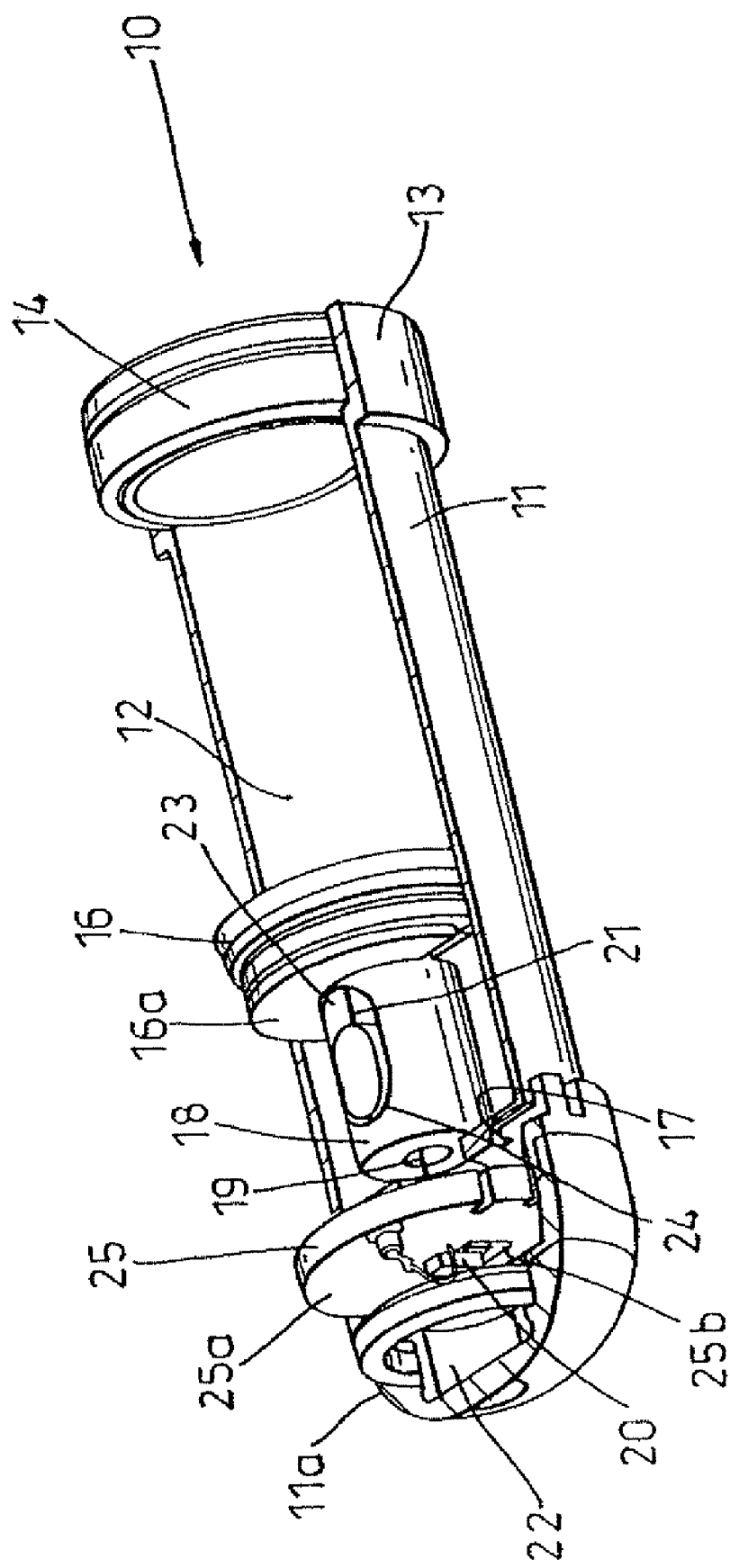
FIG. 1 is a perspective, partly sectioned view of an ingestible device according to the invention.

Referring to the drawings there is shown an ingestible device 10 according to the invention.

The overall envelope of the device 10 has been designed to be compatible with swallowing and smooth passage through the GI tract. To support this requirement the outer housing 11 of device 10 is smooth with no sharp edges and preferably has at least one end rounded as shown at 11a to facilitate swallowing. The diameter of the capsule preferably does not exceed 12 mm and the length preferably does not exceed 35 mm. The precise dimensions represent an optimisation between overall capsule size and the volume of a drug containing reservoir 12. In a preferred embodiment of the invention for a drug volume of 1.1 ml the reservoir 12 has a diameter of 11 mm and length 32 mm. The rounded end 11a can within the scope of the invention range between a hemispherical profile and a flat end with a 2 mm radius corner.

Reservoir 12 has a cylindrical interior and is open at one end 13 located at the opposite end of device 10 to rounded end 11a. Before use of the device 10 open end 13 of reservoir 12 is sealed against leakage of the contents of the hollow interior of reservoir by a closure member in the form of bung 14. Bung 14 is removable from open end 13, in a manner described below, to permit expulsion of the contents from the interior of reservoir 12. Thus if reservoir 12 is charged, before insertion of bung 14 with a substance which may be eg. in liquid or powder form, the substance may be released into the GI tract on operation of the device as described below.

The removal of bung 14, in use of the apparatus in the GI tract of a mammal, from open end 13 is by virtue of selectively controlled pressurising of the interior of reservoir 12.

This is achieved through the action of an actuator mechanism in the form of a cylindrical piston 16 that is sealingly slideable along the interior of reservoir 12 under power from an energy source (eg. a stored energy device that is, for clarity, omitted from FIG. 1).

The interior of device 10 on the side of piston 16 remote from reservoir 12 is generally hollow. Thus the energy source may in preferred embodiments take the form of a compressed spring whose spring force acts between eg. the rear face of piston 16 and a shoulder defined by an annular or part-annular rib 17 that is integral with and hence fixed relative to the housing 11.

The hollow interior of device 10 includes a shaped space or recess 22 for receiving a radioisotope tag (not visible in the drawings) that may be used for tracking progress of the device 10 along the GI tract, eg. using per se known Gamma scintigraphy techniques.

The device 10 includes a releasable latch that operates to latch the energy source in a potential energy state until a chosen time.

In the FIG. 1 embodiment the latch is in the form of an anchor 18, secured relative to piston 16, for a thread 19 made of or at least including a sharp melting point material and a heater 20 whose function is to heat the thread and melt it or at least cause a dramatic increase in its ductility at a chosen time.

More specifically, in the preferred embodiment anchor 18 includes a tubular sleeve 21 one end face of which is rigidly secured to the rear face 16a of piston 16, such that the elongate axis of sleeve 21 is generally perpendicular to rear face 16a.

The hollow interior of sleeve 21 opens at the end of sleeve 21 remote from piston 16.

Sleeve 21 includes an elongate perforation 23, whose elongate axis is generally parallel to the elongate axis of sleeve 21, passing through the wall of sleeve 21 as shown. A similar perforation passes through the wall of sleeve 21 on the opposite side thereof.

An elongate cylindrical anchor member 24 is slideably received at either end in the respective perforations, whereby the elongate axis of the anchor member is generally perpendicular to the elongate axis of the sleeve 21.

The diameter of anchor member 24 is less than the width of each perforation, whereby anchor member may be slid into place as shown, during assembly of device 10.

Anchor member 24 has firmly secured thereto one end of thread 19. Thread 19 passes through the hollow interior of sleeve 21 and emerges at the free end thereof, from where it passes through an aperture 25b in a printed circuit board (pcb) 25. Pcb 25 is in the form of a disc secured against the side of annular rib 17 remote from reservoir 12. Thread 19 is firmly secured to the surface 25a of pcb that is remote from reservoir 12. Surface 25a also mounts heater 20 in the form of a resistor. Thread 19 passes over heater 20 between the aperture and the attachment point of thread 19 to the pcb 25a.

If as disclosed hereinabove a compression spring (not shown in FIG. 1) acts between the rib 17 and piston 16, on assembly of device 10 sleeve 21 will be forced, by virtue of its attachment to piston 16, towards reservoir 12 until anchor member 18 engages the end of each perforation 23 remote from piston 16, causing thread 19 to become taut and thereby preventing the further travel of piston 16 towards bung 14 while thread 19 is intact. The tension in thread 19 draws pcb 25 hard against rib 17, thereby optionally obviating the need for further restraint of pcb 25.

Pcb 25 includes a tuned receiver of externally applied radiation whereby on the device passing through an electromagnetic field of the frequency to which the receiver is tuned, a current is induced that is fed to resistor heater 20. The heat from the heater 20 melts or renders highly ductile the thread 19, whereby piston 16 becomes free to move towards bung 14 powered by the energy stored in the spring.

Regardless of whether the substance in reservoir 12 is a liquid, a suspension, a solution a powder or even, in some embodiments of the invention, a solid, the action of piston 16 pressurises the interior of reservoir 12 until bung 14 is forced partly or completely out of open end 13 of reservoir 13. The substance when in solid form may include, but is not limited to, mini-tablets, pellets and cyclodextrin complexes, especially cyclodextrin complexes supporting further substances.

Since the interior of reservoir 12 is by then pressurised its contents are then expelled rapidly from within the device 10.

Thus if the electromagnetic field is applied when the device 10 is, following ingestion via the oesophagus, at a preferred location in the GI tract, site-specific drug delivery may be readily and rapidly achieved using a simple, reliable mechanism.

Figure 2A:
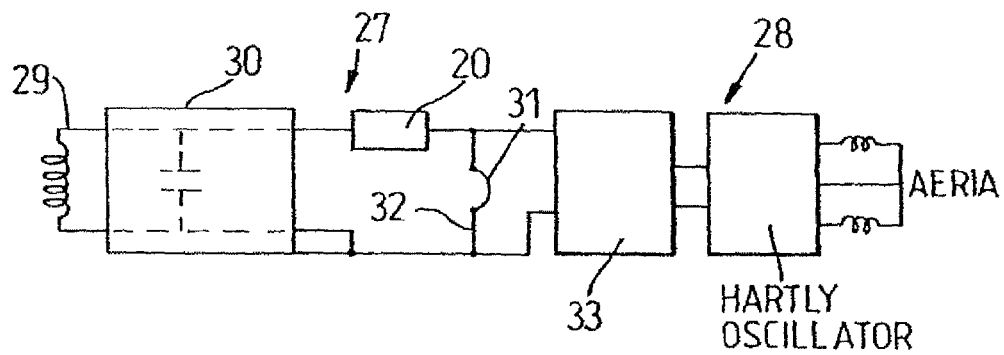
FIGS. 2a and 2b are, respectively, block diagram and schematic views of a receiver-transmitter circuit forming part of the FIG. 1 device.
Figure 2B:
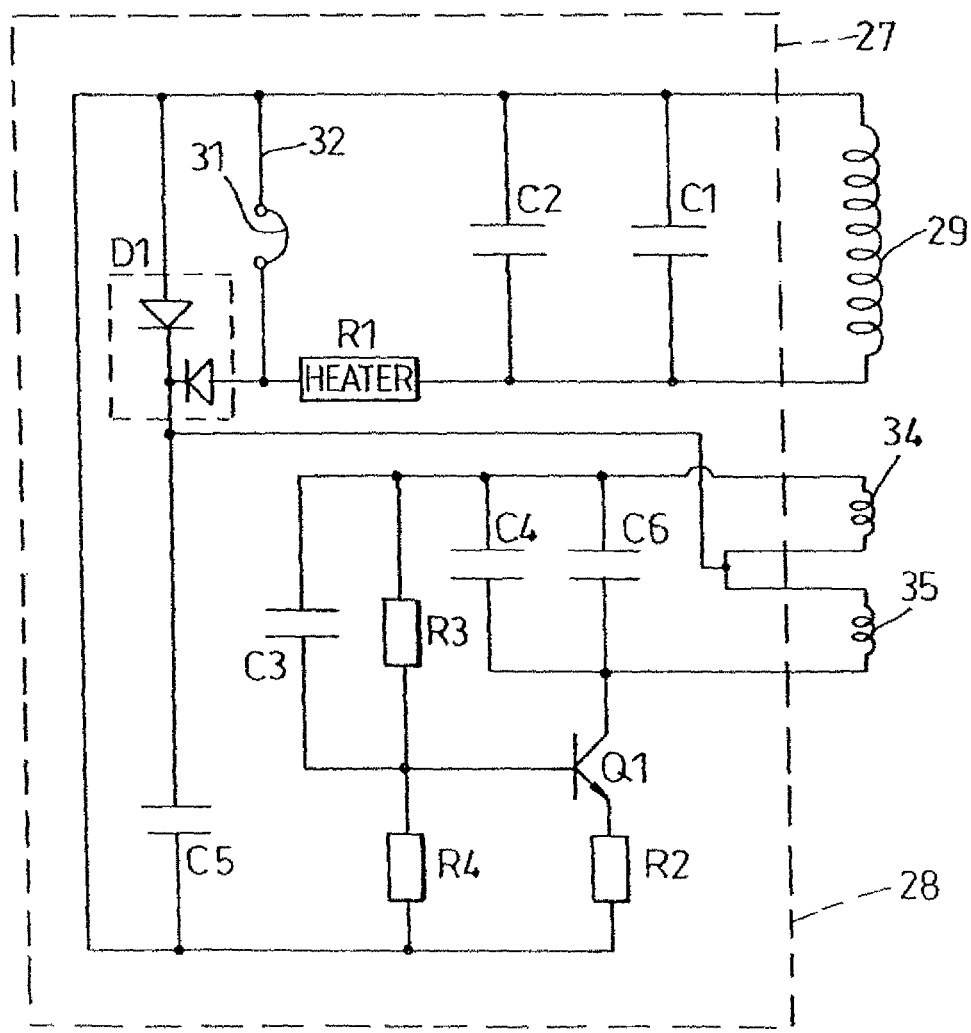

FIGS. 2a and 2b show the receiver and transmitter circuits 27, 28 of device 10 in more detail.

The receiver includes a coupling coil 29, described in more detail below, designed to couple as much energy as possible from a magnetic field incident on the device 10 while it is in the GI tract.

Coil 29 is connected to a tuner 30, that tunes the resonant frequency of the receiver and includes one or more tuning capacitors C1, C2 connected in parallel in a per se known manner.

Tuner 30 is connected in series with resistor $R_1$ defining heater 20 that is mounted on the surface 25a of pcb 25, in contact with thread 19.

In the initial condition of the device 10 resistor $R_1$ is connected in series with the remainder of receiver circuit 27 by means of a short circuit line 32 including a breakable link 31.

Pcb 25 also includes a transmitter 28.

Transmitter 28 includes a rectifier 33 that rectifies the oscillating currents in receiver 27 when the transmitter becomes operational. Transmitter 28 includes a per se known Hartly oscillator including oscillator feedback capacitor $C_3$; transmitter frequency determining capacitors $C_4$ and $C_6$; d.c. supply capacitor $C_5$; biasing resistors $R_2$, $R_3$ and $R_4$; and switching transistor $Q_1$. The outputs of the frequency determining parts $C_4$, $C_6$ of the oscillator are transmitted externally of the mammal by series antennae 34, 35. Transmitter 28 may optionally include a transmitter coil similar to or constituted by coil 29.

Line 32 initially isolates transmitter 28 from any current induced in receiver 27, until breakable line 31 is broken in a manner described below. At that point direct current, rectified by rectifier 33, flows in transmitter 28 and produces an oscillating output by virtue of the presence of the Hartly oscillator circuit.

The values of receiver tuning capacitors $C_1$ and $C_2$ and the oscillator frequency determining capacitors $C_4$ and $C_6$ are chosen so that the resonant frequency of receiver circuit 30 is distinct from the output frequency of the transmitter 28, thereby avoiding confusion between the fields input to and output by the device 10.

Figure 3:
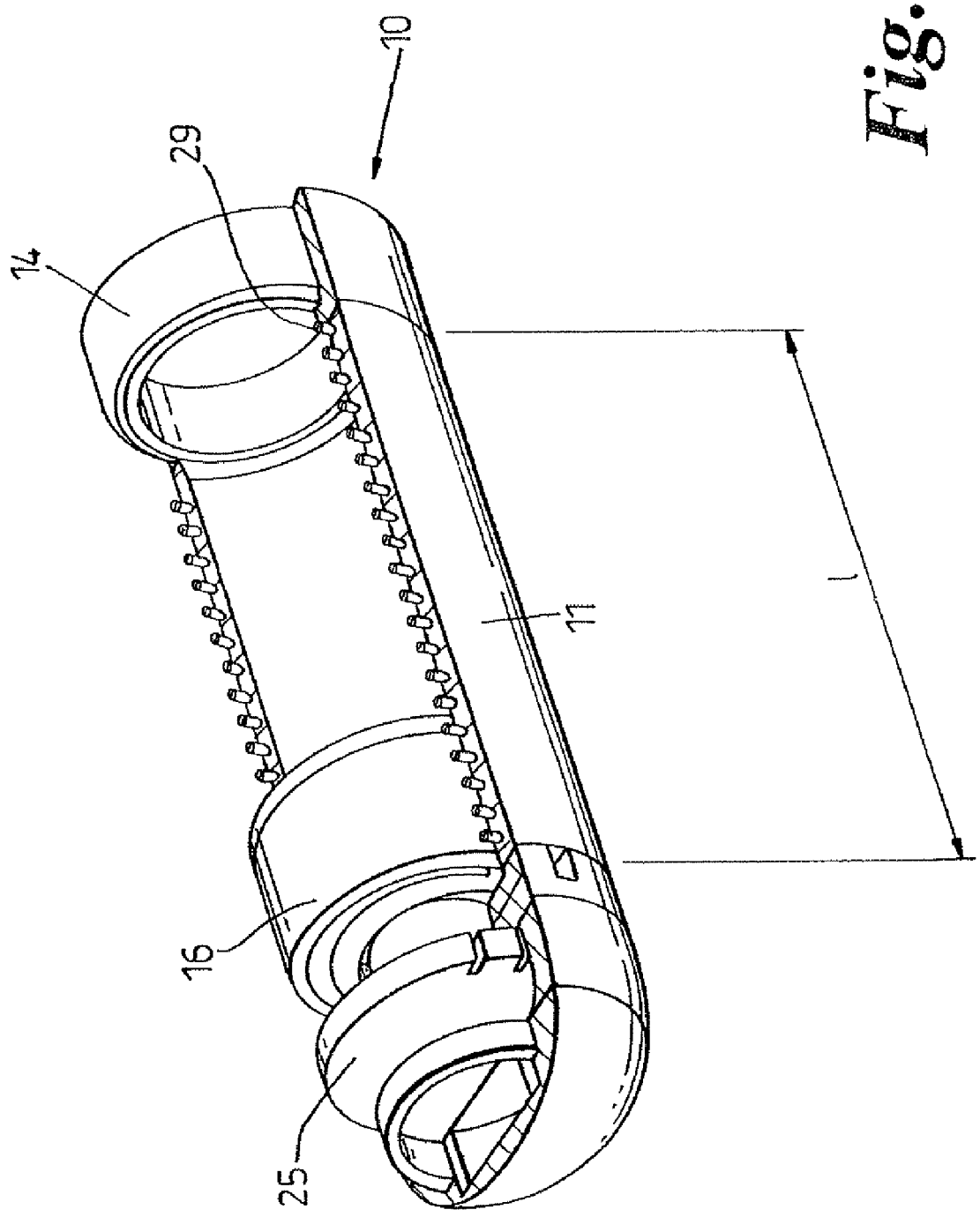
FIG. 3 shows one embodiment of antenna for use in the FIG. 1 device, including an antenna wire coiled about the capsule wall.

Referring now to FIG. 3 one arrangement of the receiver coupling coil 29 is shown, in which the coiled antenna wire 29 is embedded in the cylindrical outer wall of the housing 11 of the device 10. This arrangement is advantageously space-efficient and provides an air core for the wire 29.

In the preferred embodiment of the invention the diameter of the coil defined by wire 29 is 8-12 mm; and the length 1 from one end to the other of the coil is 10-20 mm. The preferred wire diameter is 0.1 mm-0.3 mm and the antenna coil preferably has 60-100 turns.

Figure 4:
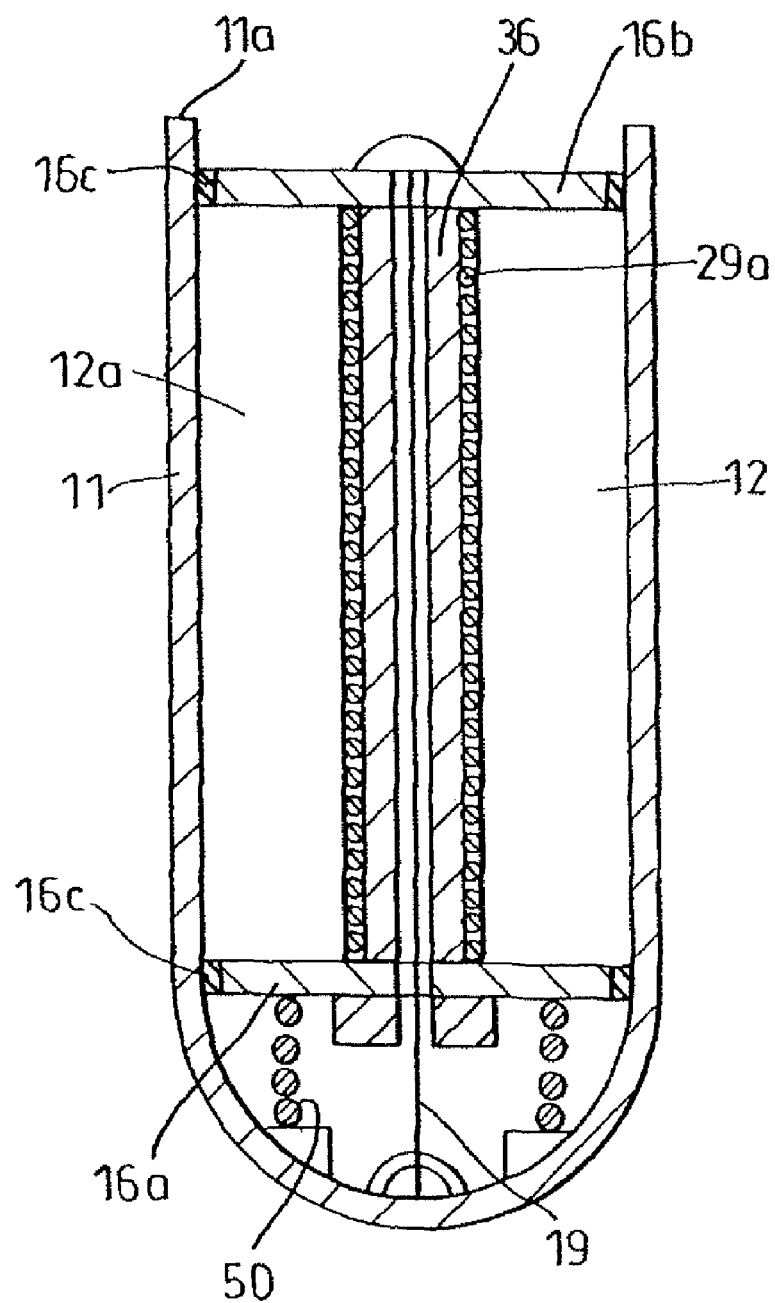
FIG. 4 shows an alternative antenna, including an antenna wire coiled about a ferrite core within the device.

FIG. 4 shows an alternative embodiment of the device 10 of the invention, in which the receiver coil 29a includes a ferrite core 36.

The ferrite core and coil form a central axial rod rigidly connecting the two discs 16a, 16b to define a bobbin-like member. The discs 16a, 16b have sliding seals 16c that slide along the hollow interior of the capsule body. The space between the discs 16a, 16b forms the reservoir 12 for the substance 12a to be dispensed. The disc 16a adjacent to the pcb 25 acts as the piston and the disc 16b at the other end acts as a cap. A compression spring 50 acts between pcb 25 and disc 16a and tends to drive the bobbin-like structure out of the openable end 11a of the housing 11. A latch and actuator mechanism similar to those of FIG. 1 temporarily prevent expulsion of the bobbin-like structure and hence the substance 12a, in a manner similar to that described hereinabove in relation to FIG. 1.

The tuning components and the latch mechanism are mounted on the bobbin separated from the substance to be released by the lower disc and seal or may be on the capsule body 11 and connected to the bobbin by fine wires. After the latch is activated and the spring 50 is released the whole of the bobbin is slid out of the open capsule end. This avoids the need to pressurise the capsule to push off the cap.

Since the ferrite core 36 couples the magnetic flux more efficiently than the air core shown in FIG. 3, the coil 29a in FIG. 4 can be made of smaller diameter than the FIG. 3 coil. Consequently the ferrite-cored coil 29a may be located as a discrete component within housing 11, as shown.

Regardless of the precise design of the coil 29, the loops thereof preferably are spaced from any fluid within or surrounding the device by a distance of 0.1 mm to 1 mm. This minimises the capacitance effects of neighbouring fluids while maintaining compactness of the device 10. The ferrite core (when present) may be similarly isolated from fluids. The isolation may arise because of a coating on the outer surface of the coil/core combination 29a, 36 of FIG. 4.

In the FIG. 4 embodiment the ferrite core 36 includes an axial bore. The thread 19 extends along the bore and is anchored as shown to disc 16b.

Figure 5A:
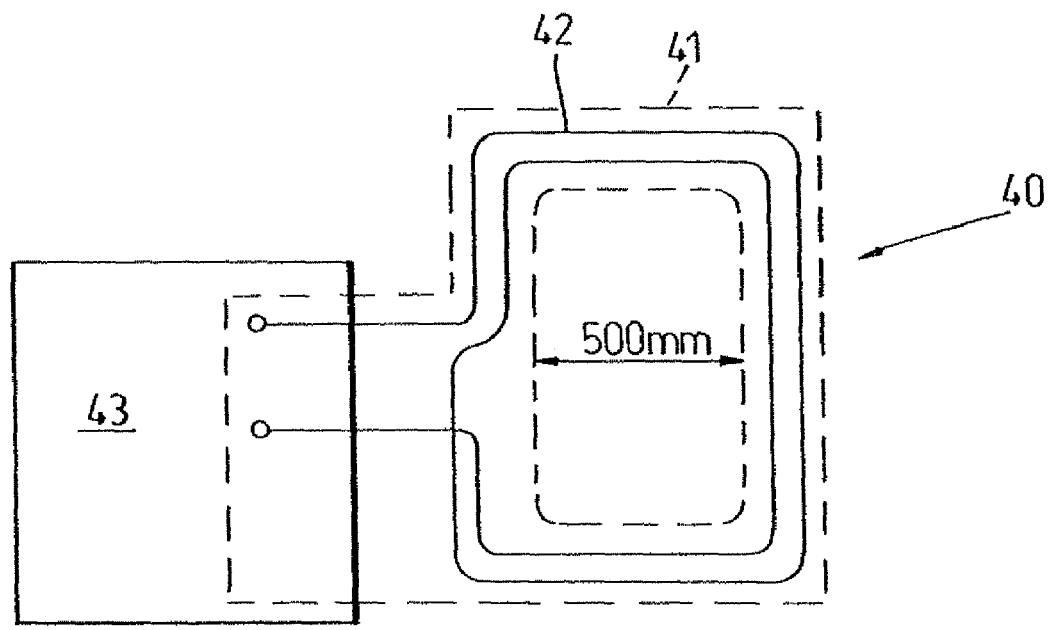
FIGS. 5a and 5b are, respectively, side elevational and plan views of an apparatus, according to the invention, for generating an oscillating, axial magnetic field.
Figure 5B:
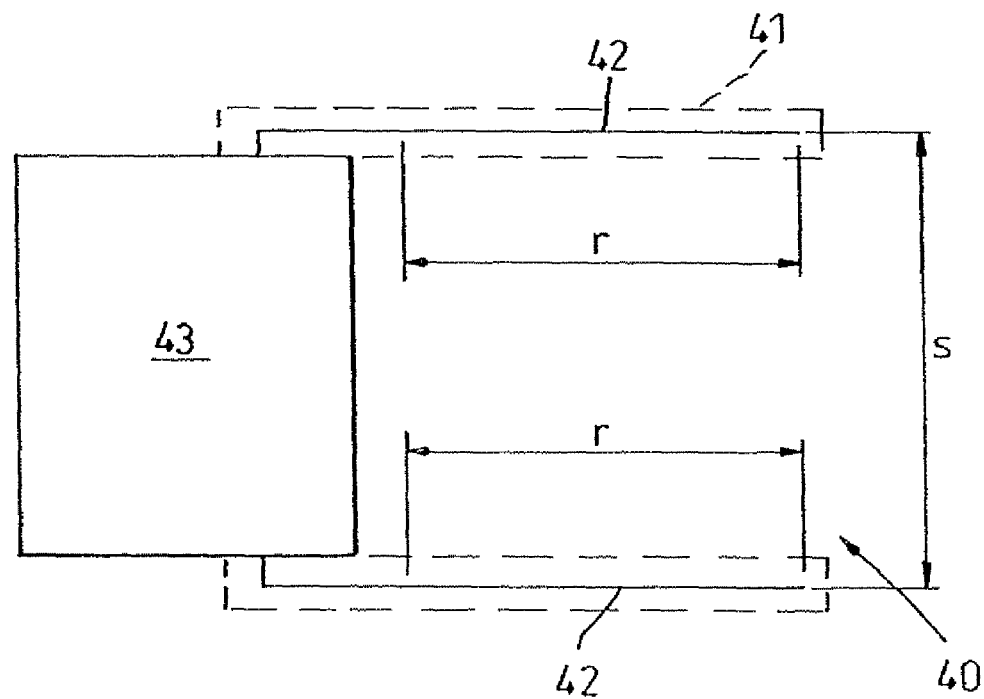

FIGS. 5a and 5b show a simplified form of an external field generator 40 according to the invention for transmitting power to a device such as, but not limited to, device 10 of FIG. 1.

The field generator 40 includes a support in the form of a box-like housing 41 for each of a pair of field coils 42.

The pair of coils 42 are in juxtaposition to one another and preferably but not essentially are dimensioned to define a Helmholtz pair. The location of and the spacing between the coils are such that, on positioning of a mammal between the coils, the coils lie on opposite sides of the abdomen of the mammal.

The coils 42 are each connected to a source of oscillating electrical energy in the form of oscillator 43.

Thus a device 10 in the GI tract can be activated by the field generator 40 when the abdomen of the mammal is between the juxtaposed coils 42 and the oscillator switched on.

The radius r of each coil 42 is the same in the preferred embodiment shown. The spacing s between the coils is between one and four times, and especially twice, the radius r. In the FIG. 5 embodiment s is approximately 500 mm, but other embodiments in which 400<s<800 mm are believed to offer good field generation while providing sufficient space between the coils 42 to accommodate the mammal. Obviously when the spacing s does not equal the radius r, the coils do not function as a Helmholtz pair.

The foregoing features confer advantages as disclosed hereinabove.

As noted hereinabove, the field generator 43 preferably generates a field that oscillates in the frequency range 1 MHz-14 MHz, and more preferably in the range 1 MHz-3 MHz.

The field coils generate, inter alia, a near field magnetic field. This has a large energy content which is continually being exchanged between the field and the current in the coils. However, apart from resistive losses, no power is used to maintain this field until the receiver coil interacts with the field to extract energy. In this way the system is more like an air cored transformer rather than a radio transmitter.

The housings 41 for the coils 42 optionally include shielding. The function of the shielding is to provide a primary safety earth screen around the field coils to protect persons touching any exposed conductors resulting from mechanical damage to the insulation. The shielding is such as to avoid forming closed loops through which the field passes since these will induce current flow and reduce the field levels generated by the coils.

The shielding may also be used to reduce the magnitude of the electric field outside the shielding generated by the coils and also the radio wave that is generated along with the magnetic field. This is advantageous in reducing any effect on other electronic equipment in the vicinity of the device. Should additional shielding be required then the coils, the oscillator and the user of the capsule could all be contained within an earthed mesh containment room or cubicle.

In addition the driver circuit for the coils 42 may include a capacitor oscillator that is separately connectable to each of the coils when the current supply to it is switched off. The inclusion of such an oscillator changes the resonant frequency of the said coil, thereby reducing or preventing resonance coupling from a further said coil when the generator is active to energize the further coil.

Figure 6:
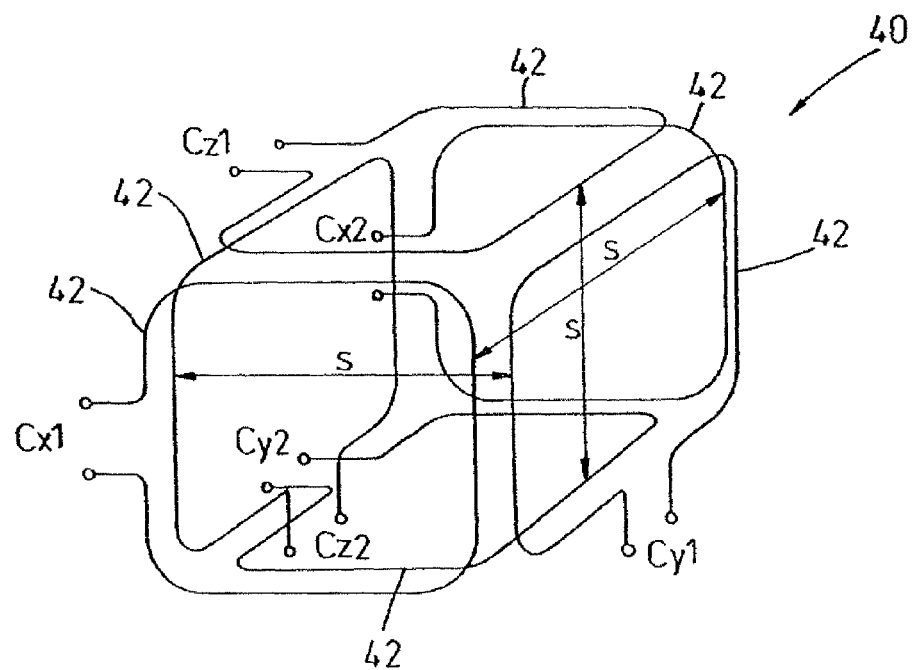
FIG. 6 shows, schematically, a preferred embodiment of oscillating field generator.

Referring now to FIG. 6 there is shown a further, and presently more preferred, embodiment of field generator 40 in which there are three pairs of the field coils 42. In FIG. 6 the pairs are arranged to generate three mutually skewed, and, more particularly, mutually orthogonal oscillating magnetic fields, by virtue of arrangement of the coils as faces of a cube.

The pairs of coils are in FIG. 6 labelled according to the following key:

| Coil | Cube Face |
|---|---|
| $C_{z1} + C_{z2}$ | top and bottom faces |
| $C_{x1} + C_{x2}$ | side faces |
| $C_{y1} + C_{y2}$ | front and back faces |

To enable a person to stand within the coils a spacing s between juxtaposed coils 42 of between 400 mm and 800 mm is appropriate.

In the FIG. 6 embodiment the respective coils 42 may if desired be secured in a framework, that may also if desired support the shielding visible in FIG. 5, whereby a mammal may stand, sit or lie in the region between the coils.

The framework may support at least one of the coils in a moveable fashion (eg. in a removable or hinged door or panel). This facilitates access to the inter-coil space, and in some embodiments permits adjustment of the spacing between the coils 42.

The framework is omitted from FIG. 6 for clarity.

Figure 7:
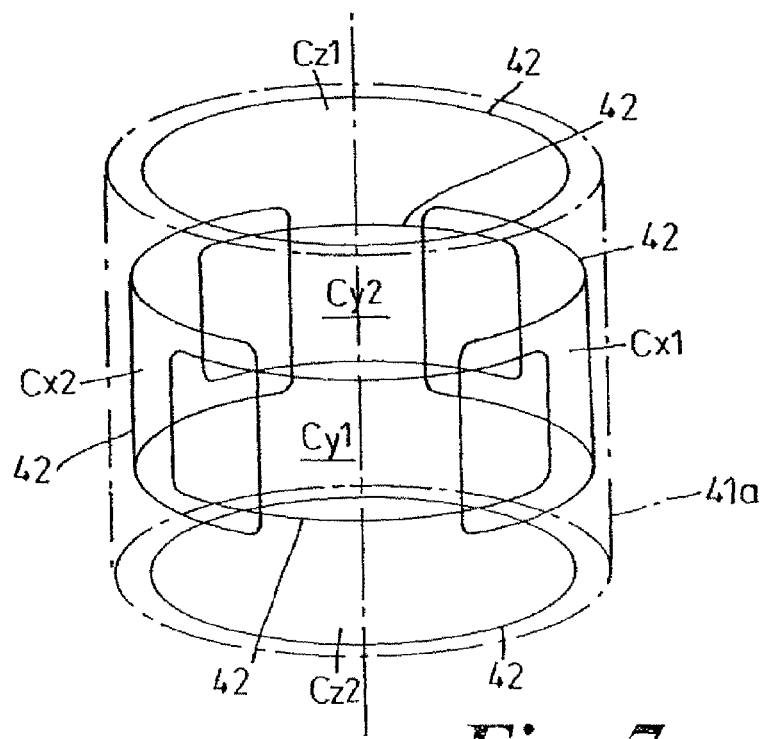
FIG. 7 shows a further embodiment of oscillating field generator according to the invention.

In FIG. 7 there is shown another arrangement of the coils 42. In FIG. 7 the components are functionally similar to their counterparts in FIG. 6, but the coils of pair $C_{z1}$, $C_{z2}$ are formed as flat circular coils, whereas the coils $C_{x1}$, $C_{x2}$, $C_{y1}$ and $C_{y2}$ define arcuate planes that confer on the coil array as a whole a hollow cylindrical shape. This arrangement of coils may be supported on a frame as in the FIG. 6 embodiment; or may if desired be supported on a wearable garment 41a schematically illustrated by dotted lines in FIG. 7.

Regardless of the precise arrangement of the coils the embodiments of FIGS. 6 and 7 generate three mutually orthogonal, oscillating magnetic fields the flux lines at least one of which will intersect the antenna 29 of the device 10, regardless of the orientation of the device 10 in the GI tract. Thus the energy in the magnetic field is efficiently transmitted to the device 10 to power its operation.

The field generators of FIGS. 6 and 7 may of course include a said capacitor oscillator separately connectable to a respective said coil 42 to prevent resonance coupling when the field generator is switched off.

The coils 42 in the preferred embodiments each include eg. 1-4 turns of a large diameter (6 mm diameter) hollow copper conductor with a wall thickness of 1 mm.

Figure 8A:
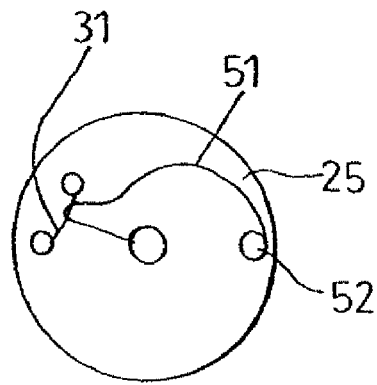
FIGS. 8a and 8b are, respectively, plan and cross-sectional views of a restraint and switch combination, according to the invention, before actuation of the switch.
Figure 9A:
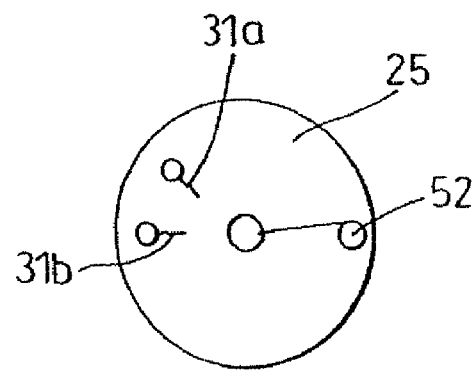
FIGS. 9a and 9b are views, corresponding to the FIG. 8 views, after actuation of the switch.
Figure 8B:
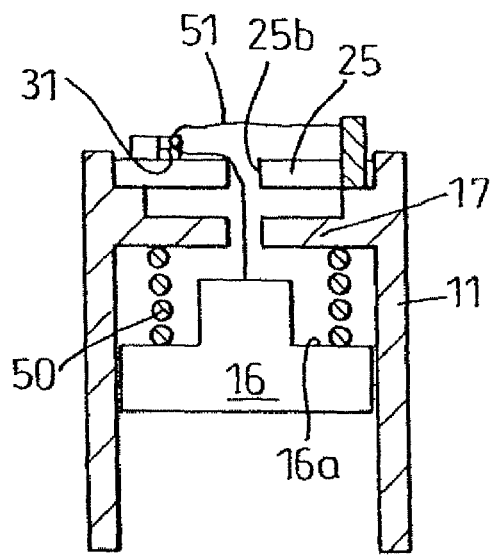
Figure 9B:
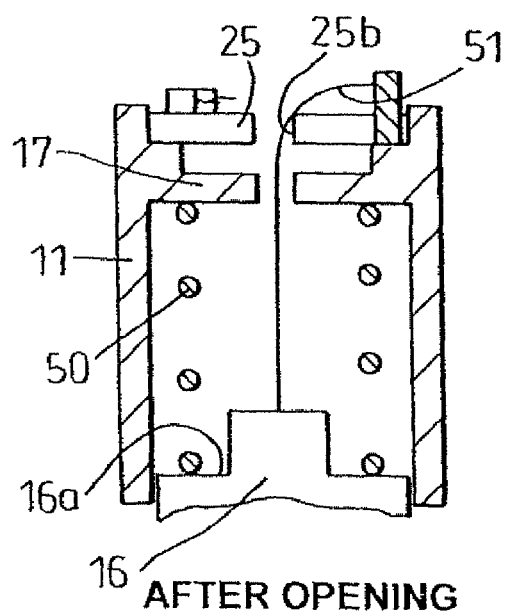

FIGS. 8 and 9 show a mechanism, in accordance with the invention, for initiating transmission of a signal, by transmitter 28, indicative of discharge of the substance from reservoir 12 into the GI tract.

FIGS. 8 and 9 show some of the components of device 10 (with others removed for clarity) in the vicinity of piston 16 and pcb 25.

FIGS. 8 and 9 schematically show the spring 50 (not visible in FIGS. 1 and 2), that acts between rib 17 and the rear face 16a of piston 16 to provide an on-board energy source for powering movement of piston 16, in respectively its compressed (FIG. 8) and uncompressed (FIG. 9) conditions.

Sharp phase change thread 19 and heater resistor 20, forming part of the thermally actuated latch arrangement visible in FIG. 1, are omitted from FIGS. 8 and 9. However, the effect of delatching of the latch is evident in these figures in the release of the spring 50 to drive the piston 16.

A restraint, in the form of a further, essentially non-fusible thread 51, interconnects rear face 16a of piston 16 and rear face 25a of pcb 25, by passing through central aperture 25b of pcb 25.

Non-fusible thread 51, on exiting aperture 25b on rear face 25, is looped through the wire defining breakable link 31 shown schematically in FIG. 2. Non-fusible thread 51 is firmly anchored to rear face 25a at a location 52 spaced laterally from breakable link 31. When thread 19, which may also pass through aperture 25b as shown in FIG. 1, is taut as shown in FIG. 1, non-fusible thread 51 is loose as a result of being significantly longer than thread 19.

When thread 19 fuses and releases the energy in spring 50, thread 51 rapidly tightens. As it does so it moves laterally in the vicinity of breakable link 31 so that it instantaneously ruptures link 31 to form unconnected link parts 31a and 31b (FIG. 9a). This connects the transmitter and receiver circuits together as previously described, so that the device 10 emits a signal indicative of expulsion of the substance from reservoir 12.

The amount of slack in thread 51 in the pre-expulsion condition (FIG. 8) is adjustable by choosing the length of thread 51. Thus the precise moment of rupturing of link 31, corresponding to a chosen point in the travel of piston 16, is adjustable.

The thread 51 may also serve as a limit or restraint to movement of the piston 16, in the sense that when thread 51 tightens as shown in FIG. 9 it prevents further movement of piston 16. This ensures that piston 16 and spring 50 are retained within device 10 even after expulsion of the substance.

Where thread 51 is used both to rupture the link and restrain the piston a means is required to set the amount of movement of the piston which causes the link to rupture. This may be achieved by positioning the link so that as the thread tightens the force is applied at the appropriate time; or by attaching the thread to the link with adhesive at the appropriate location. It may also be preferable to use a restraining thread which has a higher temperature tolerance than the latch thread to ensure that even if the device is kept in a high field environment for a long time after operating there is no possibility that the restraining thread could be broken by the temperatures reached. A suitable thread could be made from materials such as kevlar, tungsten or carbon fibre.

An alternative restraint for the moveable parts, of device 10, is shown in FIG. 13.

FIG. 13 shows a portion of the housing 11 of the FIG. 3 device 10 (having an air cored coil). The piston 16 is visible at the end of its travel, following expulsion of the substance 12a from within the reservoir 12.

A restraining ring 75 is secured on an inwardly directed shoulder 76 formed in the inner wall of housing 11 a short distance from the open end 13 of device 10. Ring 75 effectively reduces the diameter of the interior of housing 11, near to open end 13, to the extent that piston 16 is retained within reservoir 12 after use of the device 10.

The edge 75a of ring 75 facing piston 16 is chamfered to reduce the impact force arising from contact of the piston 16 and ring 75. The chamfer shown at 75a also applies both axial and radial forces to the piston 16.

The ring 75 may be manufactured from the same material as housing 11, in which case ring 75 may be welded, e.g., using a solvent welding technique, to the housing 11.

When the material of ring 75 differs from that of housing 11, glue bonding may be used instead to secure the ring in place.

As noted hereinabove, when the energy source is configured as a spring, it is desirable that the spring force is linear for as much of its travel as possible.

The requirement is also to achieve a specific force profile using a compression spring which cannot exceed given dimensions, as follows:

Force Profile

| Force at full compression sufficient to unstick piston | >10 N to 30 N |
|---|---|
| Force after 10 mm travel sufficient to remove the bung 14 | >5 N to 15 N |

Space Constraints

| Outer diameter | <9 mm |
|---|---|
| Inner diameter | >4 mm |
| Length (as small as possible) | <6 mm |

A number of approaches have been identified:
1. Single Compression Spring as shown in FIG. 10

Figures 10A, 10B:
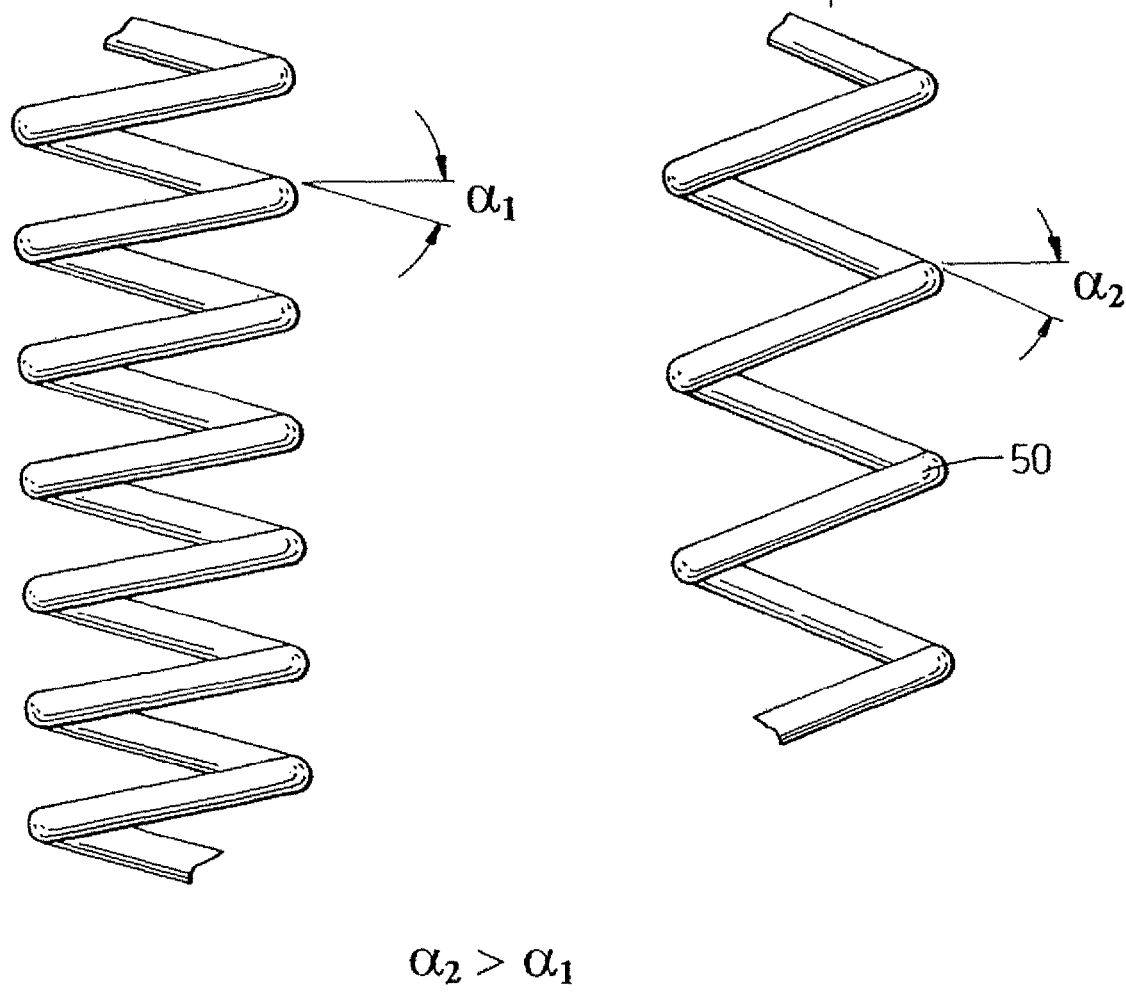

Since per se single coil spring as shown in FIG. 10a may not utilise the available space efficiently, as only the outer annulus can be used.

Since the spring only has to work once in the device 10 it can be designed with its stress load close to its yield point. The preferred spring therefore has a higher than usual helical angle and thicker wire size than available in standard springs. The FIG. 10b spring 50, according to the invention, has a helical angle $\alpha_2$ of 15° and a wire thickness t of 0.8 mm. As illustrated the angle $\alpha_2$ in the FIG. 10b spring is greater than the helical angle $\alpha_1$ of the FIG. 10a spring.

Figure 11A:
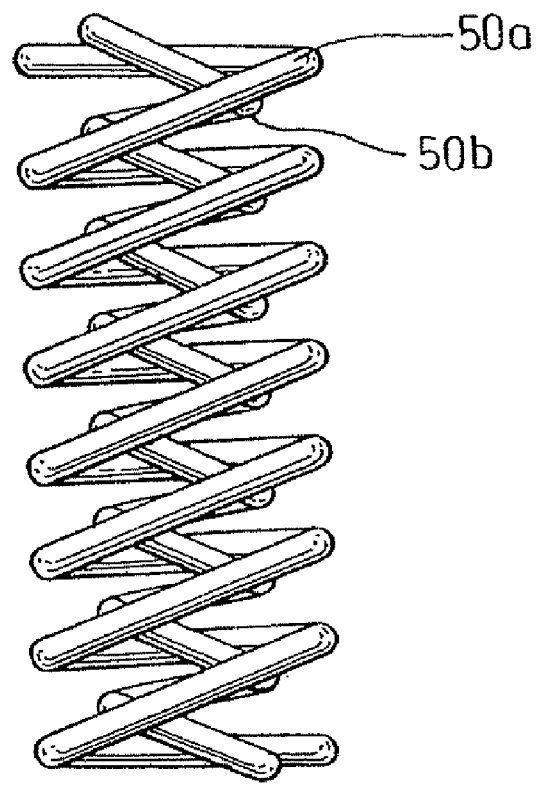

2. Two Concentric Compression Springs as shown in FIG. 11a (elevational view) and 11b (plan view)

Two compression springs 50a, 50b with one inside the other make better use of the available space. The spring diameters need to be chosen to ensure free movement relative to each other and the neighbouring parts of device 10. If the clearance is small then winding one coil clockwise and the other anti-clockwise will reduce the risk of adverse interaction between them. Spring 50a is in FIG. 11 wound clockwise and spring 50b is wound anticlockwise for this reason. Where sufficient clearance is available springs wound in the same direction could be used. This permits the use of standard springs rather than custom ones.

Figure 11B:
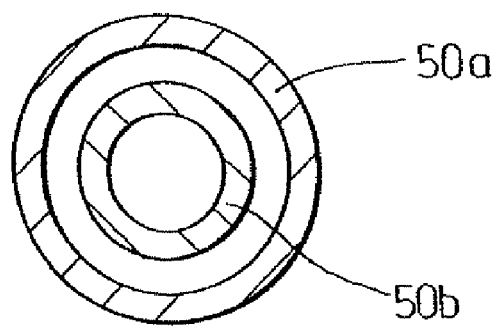
Figure 14A:
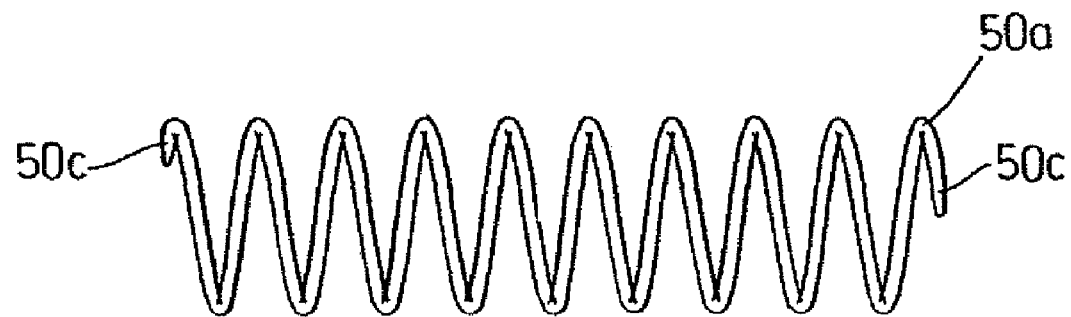
FIGS. 14a and 14b show further springs suitable for use as the energy source.
Figure 14B:
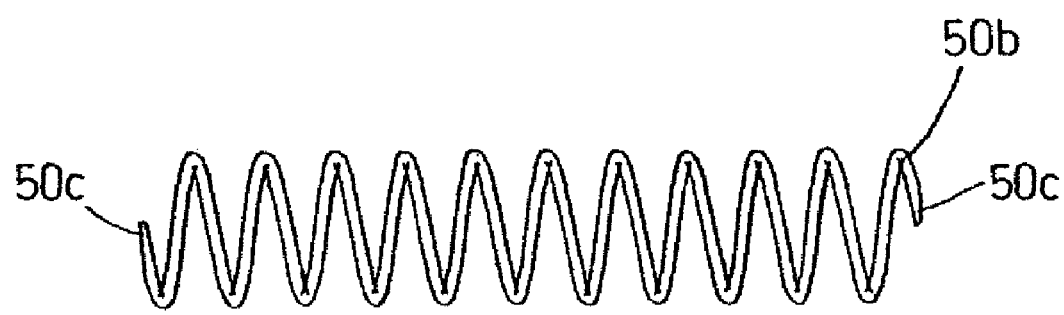

FIGS. 14a and 14b show respectively the outer spring 50a and the inner spring 50b used in a preferred form of the FIG. 11 spring arrangement.

As is conventional in compression springs, each spring 50a, 50b defines a hollow, cylinder-like shape. The inner diameter of spring 50a is greater than the outer diameter of spring 50b, whereby spring 50b is insertable with clearance into spring 50a to define a composite spring similar to that shown in FIG. 1.

The springs 50a and 50b are each wound in the same direction, and are made from so-called "piano wire" or "music wire". This material has a high energy storage characteristic suitable for use in the capsule 10.

Each spring 50a, 50b is coated with an insulator over at least part of and preferably all its length, to insulate the springs from one another in use and thereby reduce the chance of the springs creating an electrical or magnetic closed ring ("shorted turn") capable of coupling some of the energy of the electromagnetic field intended for coupling by the receiver 59.

Food grade PTFE ("Teflon"™) is the preferred coating since it is biocompatible and absorbs little of the spring energy.

The terminus 50c at each end of each wire defining a said spring 50a, 50b is truncated to ensure that the terminal coils of the springs also do not form any closed rings that would undesirably couple energy from the energized field. In addition each terminal portion 50c is ground or otherwise formed flat (ie. flush with the next adjacent coil) so that in use of the springs 50a, 50b within capsule 10 they push the piston 16 evenly and without buckling.

The springs 50a, 50b are compressible such that the compressed length of each spring is about ⅓ the length of its uncompressed state, that in the preferred embodiment is about 32 mm. These dimensions allow for a sufficiently high spring force to act over the entire length of movement of piston 16.

Figure 15:
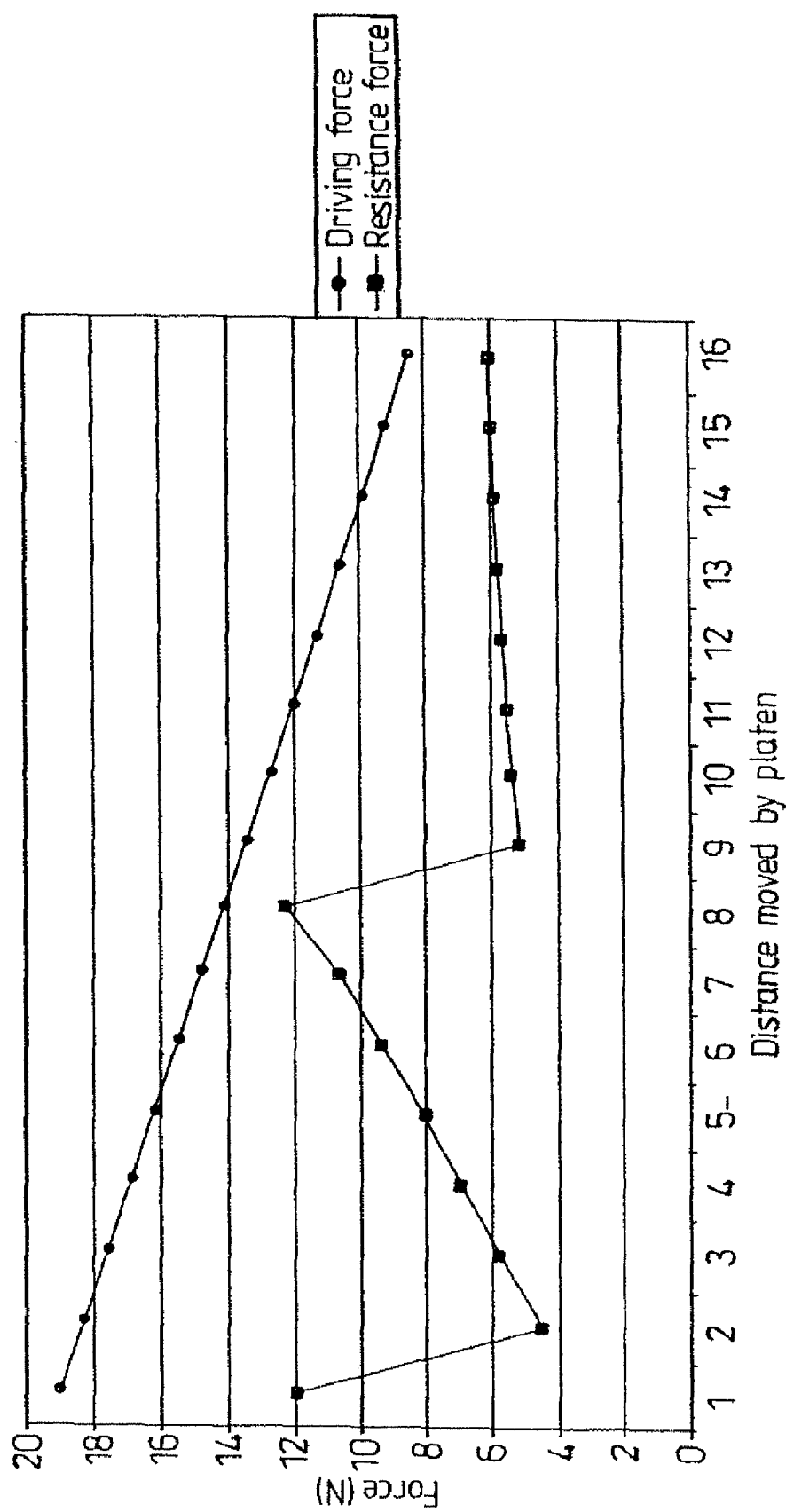
FIG. 15 is a plot comparing the force applied by springs, such as those shown in FIGS. 14a and 14b, against a force resisting opening of the reservoir of a capsule according to the invention.

FIG. 15 is a plot of the spring force applied by a composite spring such as shown in FIG. 11 or FIGS. 14a and b, against its extension. FIG. 15 also plots the resistive force offered by a bung such as bung 14 including a rolling O-ring seal. As is evident from FIG. 15, although the spring force declines during extension of the spring, during travel of the piston the spring force always exceeds the prevailing resistive force, even when the latter rises to a maximum on opening of the reservoir 12 as noted in FIG. 15.

3. Wavy Springs as shown in FIGS. 12a and 12b

Thin washers 55 plastically deformed in circumferential waves act as compression springs. Multiple washers 55 welded peak to peak as shown can given the required extension.

Performance can be superior to a coil spring in this application as more of the available space can be utilised. Thus, for example, a 0.25 mm thick annular washer with o.d. 8.5 mm and i.d. 4.5 mm could be formed to have 3 circumferential waves with a peak to peak height of 2 mm. Welding 16 of these together at their peaks in the manner shown forms a wavy spring with a compressed length of 4 mm, an extended length of 32 mm and a force profile superior to a coil spring in the available space.

FIG. 12a shows such a spring in the uncompressed state; and FIG. 12b shows the spring when it is compressed, prior to expulsion of the substance 12a from the reservoir 12.

Figure 16:
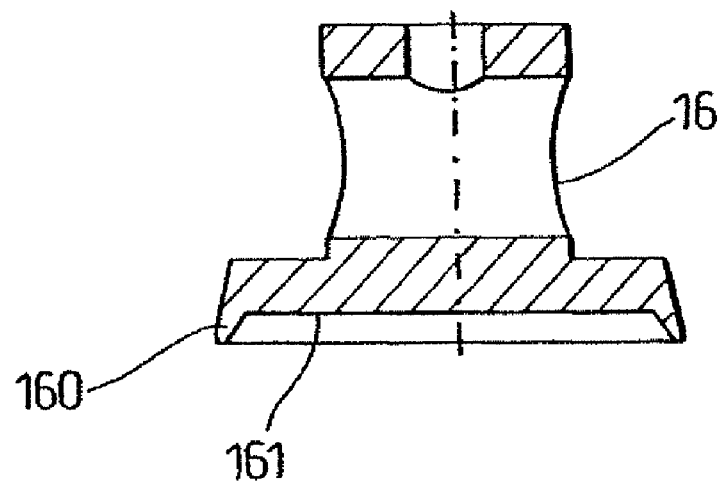
FIG. 16 is a cross sectional view of one form of piston suitable for use in the capsule of the invention.
Figure 17:
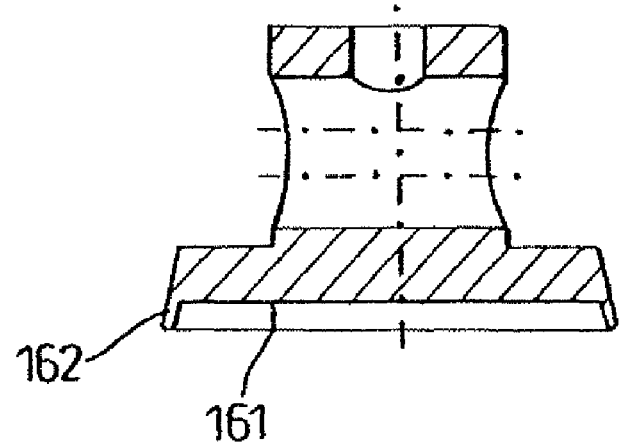
FIG. 17 is a similar view of another form of piston.

FIGS. 16 and 17 show embodiments of the piston 16 used to expel the contents of reservoir 12 of capsule 10.

The piston 16 of FIG. 16 is intended for use when the reservoir 12 is charged with a substance in liquid form.

At its end 161 facing the interior of reservoir 12 piston 16 of FIG. 16 includes an annular lip 160 that is upstanding from the periphery of end 161.

Lip 160 tapers in the direction leading away from piston 16. At least lip 160, and in practice other parts of piston 16, are formed from a flexible material whereby in use of the piston 16 the outer periphery of lip 160 slidingly sealingly engages the inner, cylindrical surface of the reservoir 12.

The tapered shape of lip 160 has been found to be particularly suited to the expulsion of liquid substances, since the lip is comparatively rigid. This confers good sealing properties, that prevent leakage of the liquid substance behind the piston.

FIG. 17 shows a similar piston 16 including a lip 162 that is parallel sided. Such a lip is particularly suited to the expulsion of powdered or granular substances, that require higher expulsion forces. The use of the parallel sided lip 162, that is more flexible than the tapered lip 160, reduces friction between the piston 16 and the reservoir 12 and hence assists expulsion of the powdered substance. Clearly when expelling a powdered substance there is a reduced need for liquid-tight sealing between the piston 16 and reservoir 12.

In both embodiments the recessed nature of face 161 relative to the lip increases the quantity of the substance containable within reservoir 12.

Figure 18:
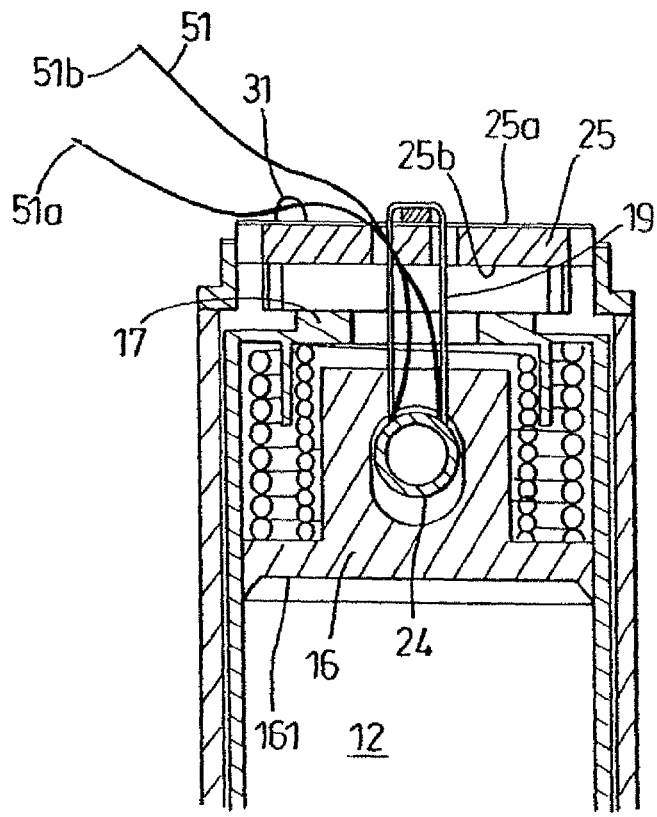
FIGS. 18 and 19 show stages in the assembly of part of a device according to the invention, including a piston such as that shown in FIG. 16 or 17; and a lost motion arrangement for breaking the breakable link on the pcb forming part of the device.
Figure 19:
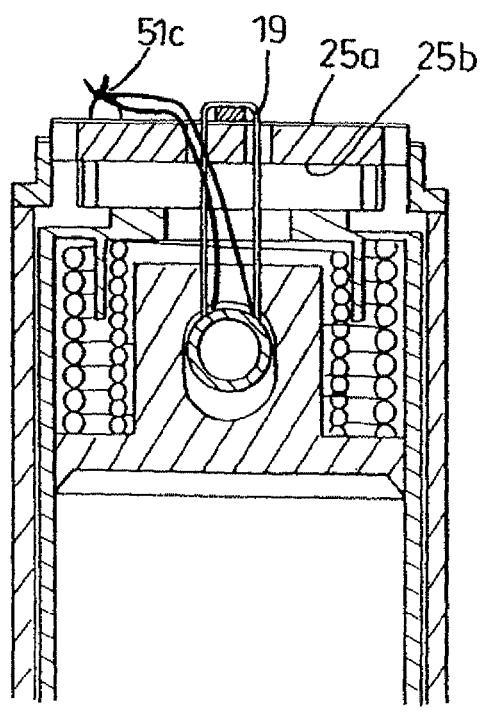

FIGS. 18 and 19 show a device, such as device 10 of FIG. 1, in a state of partial assembly in order to illustrate a lost motion arrangement for breaking the breakable link 31 of pcb 25.

As shown, device 10 has inserted in reservoir 12 a piston 16 that typically is as shown in FIG. 16 or FIG. 17.

Extending transversely through the aperture in piston 16, anchor member 24 has secured thereto the thread 19 that passes through an aperture in pcb 25 to contact heater resistor 20 on the opposite side of pcb 25 to that of piston 16.

In the partly assembled condition shown in FIG. 18 the springs 50a and 50b, that typically are as shown in FIGS. 14a and 14b, are installed reacting between the rib 17 and piston 16, thereby drawing thread 19 taut and holding pcb hard against the opposite side of rib 17.

A non-fusible thread 51, that in the preferred embodiment is made of silk, is looped around the anchor pin 24 and protrudes through the aperture in the rear face of piston 16 remote from face 161.

Both the free ends 51a, 51b of the flexible thread 51 pass through the aperture in pcb 25; and one, 51a of the ends passes under link 31 that forms a bridge interconnecting two parts of the surface of pcb 25.

Subsequently during manufacture of the device 10, the ends 51a, 51b are tied together, as shown in FIG. 19, in a firm knot 51c so that thread 51 forms a loop that is interlooped with link 31. Knot 51c is sealed with eg. cyanoacrylate or another biocompatible adhesive.

The length of thread 51 in its looped form is such that, before expulsion of the substance, the looped thread lies slack. Consequently it allows eg. 5 mm of movement of piston 16 away from pcb on melting of thread 19. Thus thread 51 and link 31 constitute a switch for switching the transmitter 28. The thread 51 is a switch member that interconnects the actuator mechanism and the switch, such that operation of the actuator mechanism causes the switch member to operate the switch.

The approximately 5 mm of free travel of the piston, before the thread 51 ruptures the link 31, constitutes a lost motion arrangement in which the slackness of looped, tied thread 51 confers the lost motion characteristic.

Figure 20:
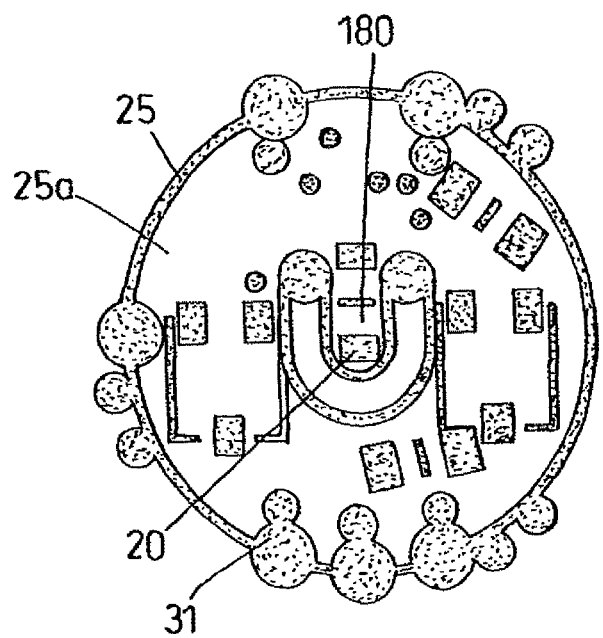
FIGS. 20 and 21 show two faces of a printed circuit board, forming part of the device, in plan view.
Figure 21:
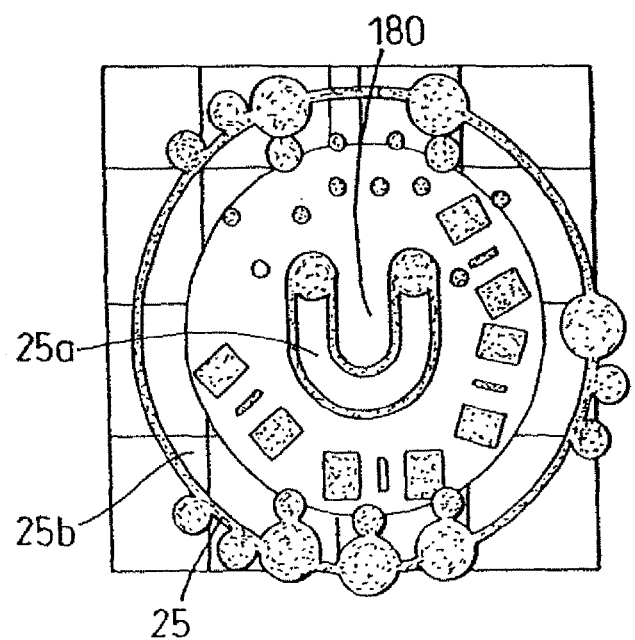

Referring now to FIGS. 20 and 21 there are shown respectively the upper and lower faces 25a and 25b of pcb 25 shown in FIGS. 18 and 19.

As is evident from FIGS. 20 and 21 the through-going aperture 25c in pcb through which flexible threads 19 and 51 pass is essentially U-shaped, defining an elongate projection 180 of pcb material.

As is evident from FIG. 20 heater resistor 20 is secured on projection 180. This arrangement facilitates assembly of the device 10 since it is an easy matter, on compression of springs 50a and 50b, to pass thread 19 over projection 180 to engage resistor 20.

As is evident from the labelling of the components in FIGS. 20 and 21 the resistors of the receiver and transmitter lie respectively on opposite surfaces 25a and 25b of pcb 25. This assists in dissipation of heat from the pcb. Of further assistance in dissipating heat is the perforating of the pcb 25 in the vicinity of each resistor.

In use of the device 10 the reservoir 12 is charged with a substance to be released and the latch set. These steps can take place during or after manufacture of the device 10, depending on the precise design of the device and its intended use.

Following such preparation the device 10 is ingested by a mammal under investigation and its progress along the GI tract monitored, eg. using a tracking technique as disclosed herein. When the device 10 reaches a chosen location in the GI tract an apparatus such as that shown in FIG. 5, 6 or 7 is operated to activate the device 10. The device 10 expels the substance 12a from reservoir 12 and the transmitter sends a signal that may be detected and processed as desired by external circuitry.

The substance 12a typically may be a pharmaceutical whose efficacy at the chosen GI tract site is under investigation. Alternatively, in uses of the apparatus not forming part of the invention as claimed, the substance 12a may be a therapeutic or diagnostic agent.

We claim:

1. An ingestible device for delivering a substance to a chosen or identifiable location in the alimentary canal of a human or animal, comprising
    an openable reservoir, for the substance, that is sealable against leakage of the substance;
    an actuator mechanism for opening the reservoir;
    an energy source, operatively connected for powering the actuator mechanism;
    a releasable latch for controllably switching the application of power to the actuator mechanism from the energy source;
    a receiver of electromagnetic radiation, for operating the latch when the receiver detects radiation within a predetermined characteristic range; and
    a transmitter of electromagnetic radiation for transmitting a signal indicative of operation of the device,
    the said reservoir including an exit aperture, for the substance, closed by a closure member that is sealingly retained relative to the aperture, the exit aperture being openable on operation of the actuator mechanism; wherein:
    (i) the latch is thermally actuated;
    (ii) the energy source is held in a potential energy state by the latch until the latch operates; and
    (iii) the device includes a heater for heating the latch whereby, on the receiver detecting the said radiation the receiver operates to power the heater and thereby release the latch, permitting expulsion of the substance from the reservoir; characterised in that:
    the device also includes a restraint operable to limit operation of the actuator mechanism; and in that, on release of the latch, the restraint operates a switch to activate the transmitter for transmission of a said signal.

2. A device according to claim 1 wherein:
    the actuator mechanism includes a moveable member moveable under power of kinetic energy from the energy source to promote expulsion of the substance from the reservoir;
    the restraint includes a flexible member interconnecting the moveable member and an anchorage fixed relative to the remainder of the device; and
    the switch includes a breakable, electrically conductive member, the flexible member and the breakable member being mutually engageable whereby on movement of the moveable member sufficiently partly or completely to expel or initiate expulsion of the substance from the reservoir the flexible member engages and breaks the breakable member to operate the switch.

3. A device according to claim 1 wherein the actuator mechanism includes a piston moveable under power from the energy source for compressing the substance in the reservoir to promote its expulsion therefrom.

4. A device according to claim 1 wherein the transmitter includes a resonant circuit connectable to draw power from the receiver; and the breakable member is an electrical short that electrically isolates the resonant circuit from the receiver until the flexible member breaks the breakable member.

5. A device according to claim 1 wherein the length of the flexible member is such as to limit the travel of the moveable member to a chosen maximum.

6. A device according to claim 1 wherein the restraint and the switch are so dimensioned and/or located that the restraint operates the switch at a time corresponding to a predetermined amount of movement of the moveable member.

7. A device according to claim 1 the reservoir of which includes a charge of liquid, powdered or solid substance or a suspension or solution for discharge into the GI tract of a mammal.

8. A device according to claim 1, including a radioisotope tag generating radiation that is detectable for indicating the location of the device in the GI tract of a mammal.

9. An ingestible device for delivering a substance to a chosen or identifiable location in the alimentary canal of a human or animal, comprising:
    an openable reservoir, for the substance, that is sealable against leakage of the substance;
    an actuator mechanism for opening the reservoir;
    an energy source, operatively connected for powering the actuator mechanism;
    a releasable latch for controllably switching the application of power to the actuator from the energy source;
    a receiver of electromagnetic radiation, for operating the latch when the receiver detects radiation within a predetermined characteristic range; and
    a transmitter of electromagnetic radiation for transmitting a signal indicative of operation of the device;
    the said reservoir including an exit aperture, for the substance, closed by a closure member that is sealingly retained relative to the aperture, the exit aperture being openable on operation of the actuator mechanism; wherein
    (i) the latch is thermally actuated;
    (ii) the energy source is held in a potential energy state by the latch until the latch operates; and
    (iii) the device includes a heater for heating the latch whereby, on the receiver-detecting the said radiation the receiver operates to power the heater and thereby release the latch, permitting expulsion of the substance from the reservoir; characterised in that the device also includes (a) a restraint operable to limit operation of the actuator mechanism;

(b) a switch for switchably operating the transmitter; and (c) a switch member operatively interconnecting the actuator mechanism and the switch such that operation of the actuator mechanism causes the switch member to operate the said switch.

10. A device according to claim 9 wherein the actuator mechanism includes a moveable member and the switch member includes a lost motion arrangement whereby the moveable member moves before the switch member operates the switch.

11. A device according to claim 9 wherein the actuator mechanism includes a moveable member and the switch member includes a lost motion arrangement whereby the moveable member moves before the switch member operates the switch and wherein the switch member interconnects the moveable member and the switch; and includes a slack, flexible member the slackness of which provides the said lost motion arrangement.

12. A device according to claim 9 wherein the actuator mechanism includes a moveable member and the switch member includes a lost motion arrangement whereby the moveable member moves before the switch member operates the switch and wherein the switch member interconnects the moveable member and the switch; and includes a slack, flexible member the slackness of which provides the said lost motion arrangement, the device including a printed circuit board (pcb) having a breakable wire secured at spaced locations thereon to define the switch, the pcb being perforated and the said switch and the said moveable member lying respectively at opposite sides of the pcb; and the switch member including a slack, flexible filament that passes through a perforation in the pcb and including a loop that encloses the breakable wire, the filament being secured to the moveable member whereby when the moveable member moves the filament tightens such that the loop breaks the breakable wire.

13. A device according to claim 9 including a printed circuit board (pcb) supporting the receiver and the transmitter, the receiver and the transmitter each including a resistor track secured on the pcb, the resistor tracks of the transmitter and receiver lying respectively on opposite sides of the pcb.

14. A device according to claim 9 including a printed circuit board (pcb) supporting the receiver and the transmitter, the receiver and the transmitter each including a resistor track secured on the pcb, the resistor tracks of the transmitter and receiver lying respectively on opposite sides of the pcb and wherein the pcb includes one or more perforations in the vicinity of each said resistor track.

15. A device according to claim 9 wherein the actuator mechanism includes a moveable member and the switch member includes a lost motion arrangement whereby the moveable member moves before the switch member operates the switch and wherein the switch member interconnects the moveable member and the switch; and includes a slack, flexible member the slackness of which provides the said lost motion arrangement, the device including a printed circuit board (pcb) having a breakable wire secured at spaced locations thereon to define the switch, the pcb being perforated and the said switch and the said moveable member lying respectively at opposite sides of the pcb; and the switch member including a slack, flexible filament that passes through a perforation in the pcb and including a loop that encloses the breakable wire, the filament being secured to the moveable member whereby when the moveable member moves the filament tightens such that the loop breaks the breakable wire; wherein a projection protrudes from an edge of a perforation through the pcb; and wherein the latch includes a sharp melting point filament interconnecting the actuator member and the said projection.

16. A device according to claim 15 wherein the heater is secured to the projection in heat transmitting proximity to the sharp melting point filament.

17. A device according to claim 9, the reservoir of which includes a charge of liquid, powdered or solid substance or a suspension or solution for discharge into the GI tract of a mammal.

18. A device according to claim 9, including a radioisotope tag generating radiation that is detectable for indicating the location of the device in the GI tract of a mammal.

* * * * *